(12) United States Patent
Ni et al.

(10) Patent No.: US 6,893,870 B2
(45) Date of Patent: May 17, 2005

(54) PANCREAS-DERIVED PLASMINOGEN ACTIVATOR INHIBITOR

(75) Inventors: Jian Ni, Germantown, MD (US); Reiner L. Gentz, Belo Horizonte-Mg (BR); Steven M. Ruben, Brookeville, MD (US); Y. Eric Shi, Roslyn Heights, NY (US)

(73) Assignee: Human Genome Sciences, Inc., Rockville, MD (US)

( * ) Notice: Subject to any disclaimer, the term of this patent is extended or adjusted under 35 U.S.C. 154(b) by 36 days.

(21) Appl. No.: 10/628,395

(22) Filed: Jul. 29, 2003

(65) Prior Publication Data
US 2004/0086978 A1 May 6, 2004

Related U.S. Application Data

(60) Division of application No. 09/902,684, filed on Jul. 12, 2001, now Pat. No. 6,649,738, which is a division of application No. 09/026,408, filed on Feb. 19, 1998, now Pat. No. 6,303,338, which is a continuation-in-part of application No. 08/934,011, filed on Aug. 15, 1997, now abandoned.
(60) Provisional application No. 60/024,056, filed on Aug. 16, 1996.

(51) Int. Cl.$^7$ ............................................. C12N 5/02
(52) U.S. Cl. ...................................... 435/331; 435/338
(58) Field of Search ................................. 435/326, 338, 435/331; 530/388.26

(56) References Cited

U.S. PATENT DOCUMENTS

| 4,923,807 A | 5/1990 | Webb et al. |
|---|---|---|
| 5,470,970 A | 11/1995 | Sager et al. |
| 5,804,376 A | 9/1998 | Braxton et al. |
| 6,303,338 B1 | * 10/2001 | Ni et al. |
| 6,649,738 B2 | * 11/2003 | Ni et al. |

FOREIGN PATENT DOCUMENTS

WO    WO-96/34957    11/1996

OTHER PUBLICATIONS

Barton, G.J., "Protein sequence alignment and database scanning," in: Protein Structure Prediction, A Practical Approach, Sternberg, M.J.E., ed., IRL Press at Oxford University Press, Oxford, UK, pp. 31–63 (Aug. 1996).
Carrell, R.W. et al., "The Serpins; Evolution and Adaptation in a Family of Protease Inhibitors," *Cold Spring Harbor Symp. Quant. Biol.* 52:527–535, Cold Spring Harbor Laboratory (1987).
Cronshagen, U. et al., "A novel protein expressed exclusively in pancreatic cells is proposed to be a serpin," Abstract No. 247, *Eur. J. Cell Biol.* 94:83, Nature Publishing Group (1993).

Cunningham, B.C. and Wells, J.A., "High–Resolution Epitope Mapping of hGH–Receptor Interactions by Alanine–Scanning Mutagenesis," *Science* 244:1081–1085, American Association for the Advancement of Science (1989).
Fazioli, F. and Blasi, F., "Urokinase–type plasminogen activator and its receptor; new targets for anti–metastatic therapy?," *TiPS* 15:25–29, Elsevier Science (1994).
George, D.G. et al., "Current Methods in Sequence Comparison and Analysis," in: Macromolecular Sequencing and Synthesis, Selected Methods and Applications, D.H. Schlesinger, ed., Alan R. Liss, Inc. New York, NY, pp. 127–149 (1988).
Ginsburg, D. et al., "cDNA Cloning of Human Plasminogen Activator–Inhibitor from Endothelial Cells," *J. Clin. Invest.* 78:1673–1680, American Society for Clinical Investigation (1986).
Krishnamurti, C. et al., "Stimulation Of Plasminogen Activator Inhibitor Activity In Human Monocytes Infected With Dengue Virus," *Am. J. Trop. Med. Hyg.* 40:102–107, American Society of Tropical Medicine and Hygiene (1989).
Kruithof, E.K.O. et al., "Biological and Clinical Aspects of Plasminogen Activator Inhibitor Type 2," *Blood* 86:4007–4024, Journal of the American Society of Hematology (Dec. 1995).
Leiper, K. et al., "Tissue plasminogen activator, plasminogen activator inhibitors, and activator–inhibitor complex in liver disease," *J. Clin. Pathol.* 47:214–217, BMJ Publishing Group (1994).
Ngo, J.T. et al., "Computational Complexity, Protein Structure Prediction, and the Levinthal Paradox," in: The Protein Folding Problem and Tertiary Strucure Prediction, Mertz, Jr., K. and Le Grand, S., eds., Birkhauser, Boston, Massachusetts, pp. 491–495 (1994).
Robson, R. and Garnier, J., eds., "Modern ideas and notations relating to primary structure," in: Introduction to Proteins and Protein Engineering, Elsevier, Amsterdam, Holland pp. 41–43 (1986).
Rudinger, J., "Characteristics of the amino acids as components of a peptide hormone sequence," in: Peptide Hormones, Parsons, J.A., eds., University Park Press, Baltimore, Maryland, pp. 5–7 (1976).

(Continued)

*Primary Examiner*—Christina Chan
*Assistant Examiner*—Maher Haddad
(74) *Attorney, Agent, or Firm*—Human Genome Sciences, Inc.

(57) ABSTRACT

The present invention relates to a novel member of the plasminogen activator inhibitor protein family. In particular, isolated nucleic acid molecules are provided encoding the pancreas-derived plasminogen activator inhibitor protein. Pancreas-derived plasminogen activator inhibitor polypeptides are also provided as are vectors, host cells and recombinant methods for producing the same. The invention further relates to methods for treating physiologic and pathologic disease conditions and diagnostic methods for detecting pathologic disorders.

26 Claims, 10 Drawing Sheets

OTHER PUBLICATIONS

Sprecher, C.A. et al., "Molecular Cloning, Expression, and Partial Characterization of Two Novel Members of the Ovalbumin Family of Serine Proteinase Inhibitors," *J. Biol. Chem.* 270:29854–29861, American Society for Biochemistry and Molecular Biology (Dec. 1995).

Sun, J. et al., "Gene Structure, Chromosomal Localization, and Expression of the Murine Homologue of Human Proteinase Inhibitor 6 (Pl–6) Suggests Divergence of Pl–6 from the Ovalbumin Serpins," *J. Biol. Chem.* 270:16089–16096, American Society for Biochemistry and Molecular Biology (Jul. 1995).

Urano, T. et al., "A substrate–like form of plasminogen–activator–inhibitor type 1," *Eur. J. Biochem.* 209:985–992, Federation of European Biochemical Societies (1992).

Wells, J.A., "Additivity of Mutational Effects in Proteins," *Biochem.* 29:8509–8516, American Chemical Society (1990).

Genbank Report, Accession No. Z30585, submitted by Cronshagen, U. et al. (1994).

Genbank Report, Accession No. AAA6003, submitted by Ginsburg, D. et al. (Jan. 1995).

Genbank Report, Accession No. X16383, submitted by Sawdey, M.S. (Feb. 1995).

Genbank Report, Accession No. D13909, submitted by Mimuro et al. (Nov. 1995).

NCBI Entrez, GenBank Report, Accession No. T52685, from Hillier, L. et al. (Feb. 1995)

NCBI Entrez, GenBank Report, Accession No. F07041, from Auffray, C. et al. (Feb. 1995).

NCBI Entrez, GenBank Report, Accession No. D58484, from Fujiwara, T. et al. (Aug. 1995).

NCBI Entrez, GenBank Report, Accession No. H81869, from Hillier, L. et al. (Nov. 1995).

NCBI Entrez, GenBank Report, Accession No. H82168, from Hillier, L. et al. (Nov. 1995).

NCBI Entrez, GenBank Report, Accession No. D27259, from Kohara, Y. et al. (Nov. 1995).

NCBI Entrez, GenBank Report, Accession No. N34066, from Hillier, L. et al. (Jan. 1996).

NCBI Entrez, GenBank Report, Accession No. N41961, from Hillier, L. et al. (Jan. 1996).

NCBI Entrez, GenBank Report, Accession No. N86663, from Liew, C.C. (Apr. 1996).

NCBI Entrez, GenBank Report, Accession No. C18938, from Fujiwara, T. et al. (Oct. 1996).

NCBI Entrez, GenBank Report, Accession No. C18122, from Fujiwara, T. et al. (Oct. 1996).

NCBI Entrez, GenBank Report, Accession No. AA091273, from Liew, C.C. (Oct. 1996).

NCBI Entrez, GenBank Report, Accession No. AA104570, from Marra, M. et al. (Oct. 1996).

NCBI Entrez, GenBank Report, Accession No. AA147887, from Hillier, L. et al. (Dec. 1996).

NCBI Entrez, GenBank Report, Accession No. AA147909, from Hillier, L. et al. (Dec. 1996).

NCBI Entrez, GenBank Report, Accession No. AA147917, from Hillier, L. et al. (Dec. 1996).

NCBI Entrez, GenBank Report, Accession No. AA168365, from Marra, M. et al. (Feb. 1997).

NCBI Entrez, GenBank Report, Accession No. AA117151, from Marra, M. et al. (Feb. 1997).

NCBI Entrez, GenBank Report, Accession No. AA276326, from Marra, M. et al. (Apr. 1997).

NCBI Entrez, GenBank Report, Accession No. AA303966, from Adams, M.D. et al. (Apr. 1997).

NCBI Entrez, GenBank Report, Accession No. AA296389, from Adams, M.D. et al. (Apr. 1997).

NCBI Entrez, GenBank Report, Accession No. AA296506, from Adams, M.D. et al. (Apr. 1997).

NCBI Entrez, GenBank Report, Accession No. AA317566, from Adams, M.D. et al. (Apr. 1997).

NCBI Entrez, GenBank Report, Accession No. AA372832, from Adams, M.D. et al. (Apr. 1997).

NCBI Entrez, GenBank Report, Accession No. AA409232, from Ko, M.S.H. et al. (May 1997).

NCBI Entrez, GenBank Report, Accession No. AA045132, from Hillier, L. et al. (May 1997).

NCBI Entrez, GenBank Report, Accession No. AA473834, from Marra, M. et al. (Jun. 1997).

NCBI Entrez, GenBank Report, Accession No. H09005, from Hillier, L. et al. (Jun. 1997).

NCBI Entrez, GenBank Report, Accession No. AA544064, from Marra, M. et al. (Aug. 1997).

NCBI Entrez, GenBank Report, Accession No. AA146811, from Hillier, L. et al. (Aug. 1997).

NCBI Entrez, GenBank Report, Accession No. AA242969, from Hillier, L. et al. (Aug. 1997).

NCBI Entrez, GenBank Report, Accession No. AA562720, from Marra, M. et al. (Aug. 1997).

NCBI Entrez, GenBank Report, Accession No. AA542814, from NCI–CGAP (Aug. 1997).

NCBI Entrez, GenBank Report, Accession No. AA571334, from Marra, M. et al. (Aug. 1997).

NCBI Entrez, GenBank Report, Accession No. C31835, from Kohara, Y. et al. (Sep. 1997).

NCBI Entrez, GenBank Report, Accession No. AA589090, from Marra, M. et al. (Sep. 1997).

NCBI Entrez, GenBank Report, Accession No. H52450, from Hillier, L. et al. (Sep. 1995).

NCBI Entrez, GenBank Report, Accession No. AA596670, from Marra, M. et al. (Sep. 1997).

NCBI Entrez, GenBank Report, Accession No. C67391, from Kohara, Y. et al. (Sep. 1997).

NCBI Entrez, GenBank Report, Accession No. C71498, from Kohara, Y. et al. (Sep. 1997).

NCBI Entrez, GenBank Report, Accession No. AA645751, from Marra, M. et al. (Oct. 1997).

NCBI Entrez, GenBank Report, Accession No. AA666768, from Marra, M. et al. (Nov. 1997).

NCBI Entrez, GenBank Report, Accession No. AA684304, from Marra, M. et al. (Dec. 1997).

NCBI Entrez, GenBank Report, Accession No. AA706757, from Hillier, L. et al. (Dec. 1997).

NCBI Entrez, GenBank Report, Accession No. AA738996, from Marra, M. et al. (1998).

NCBI Entrez, GenBank Report, Accession No. AA487997, from Hillier, L. et al. (1998).

NCBI Entrez, GenBank Report, Accession No. AA852339, from Jia, L. et al. (1998).

NCBI Entrez, GenBank Report, Accession No. AA867587, from Marra, M. et al. (1998).

NCBI Entrez, GenBank Report, Accession No. AA869929, from Marra, M. et al. (1998).

NCBI Entrez, GenBank Report, Accession No. AA869413, from Marra, M. et al. (1998).

* cited by examiner

```
                10                          30                         50
         GGCACGAGGGAAAACTCTATTTTGAAAATGAATATATTTTGATTTAAACAATACAGAGAA
                70                          90                        110
         GTCAAAATGGACACAATCTTCTTGTGGAGTCTTCTATTGCTGTTTTTTGGAAGTCAAGCC
                  M  D  T  I  F  L  W  S  L  L  L  L  F  F  G  S  Q  A
               130                         150                        170
         TCAAGATGCTCAGCTCAAAAAAATACCGAATTTGCAGTGGATCTTTATCAAGAGGTTTCC
          S  R  C  S  A  Q  K  N  T  E  F  A  V  D  L  Y  Q  E  V  S
               190                         210                        230
         TTATCTCATAAGGACAACATTATATTTTCACCCCTTGGAATAACTTTGGTTCTTGAGATG
          L  S  H  K  D  N  I  I  F  S  P  L  G  I  T  L  V  L  E  M
               250                         270                        290
         GTACAACTGGGAGCCAAAGGAAAAGCACAGCAGCAGATAAGACAAACTTTAAAACAACAG
          V  Q  L  G  A  K  G  K  A  Q  Q  Q  I  R  Q  T  L  K  Q  Q
               310                         330                        350
         GAAACCTCAGCTGGGGAAGAATTTTTGGTACTGAAGTCATTTTGCTCTGCCATCTCAGAG
          E  T  S  A  G  E  E  F  L  V  L  K  S  F  C  S  A  I  S  E
               370                         390                        410
         AAAAAACAAGAATTTACATTTAATCTTGCCAATGCCCTCTACCTTCAAGAAGGATTCACT
          K  K  Q  E  F  T  F  N  L  A  N  A  L  Y  L  Q  E  G  F  T
               430                         450                        470
         GTGAAAGAACAGTATCTCCATGGCAACAAGGAATTTTTTCAGAGTGCTATAAAACTGGTG
          V  K  E  Q  Y  L  H  G  N  K  E  F  F  Q  S  A  I  K  L  V
               490                         510                        530
         GATTTTCAAGATGCAAAGGCTTGTGCAGACATGATAAGTACCTGGGTAGAAAGAAAAACA
          D  F  Q  D  A  K  A  C  A  E  M  I  S  T  W  V  E  R  K  T
               550                         570                        590
         GATGGAAAAATTAAAGACATGTTTTCAGGGGAAGAATTTGGCCCTCTGACTCGGCTTGTC
          D  G  K  I  K  D  M  F  S  G  E  E  F  G  P  L  T  R  L  V
               610                         630                        650
         CTGGTGAATGCTATTTATTTCAAAGGAGATTGGAAACAGAAATTCAGAAAAGAGGACACA
          L  V  N  A  I  Y  F  K  G  D  W  K  Q  K  F  R  K  E  D  T
               670                         690                        710
         CAGCTGATAAATTTTACTAAGAAAAATGGTTCAACTGTCAAAATTCCAATGATGAAGGCT
          Q  L  I  N  F  T  K  K  N  G  S  T  V  K  I  P  M  M  K  A
               730                         750                        770
         CTTCTGAGAACAAAATATGGTTATTTTTCTGAATCTTCCCTGAACTACCAAGTTTTAGAA
          L  L  R  T  K  Y  G  Y  F  S  E  S  S  L  N  Y  Q  V  L  E
               790                         810                        830
         TTGTCTTACAAAGGTGATGAATTTAGCTTAATTATCATACTTCCTGCAGAAGGTATGGAT
          L  S  Y  K  G  D  E  F  S  L  I  I  I  L  P  A  E  G  M  D
               850                         870                        890
```

FIG.1A

```
ATAGAAGAAGTGGAAAAACTAATTACTGCTCAACAAATCCTAAAATGGCTCTCTGAGATG
 I  E  E  V  E  K  L  I  T  A  Q  Q  I  L  K  W  L  S  E  M
        910               930                950
CAAGAAGAGGAAGTAGAAATAAGCCTCCCTAGATTTAAAGTAGAACAAAAAGTAGACTTC
 Q  E  E  E  V  E  I  S  L  P  R  F  K  V  E  Q  K  V  D  F
        970               990                1010
AAAGACGTTTTGTATTCTTTGAACATAACCGAGATATTTAGTGGTGGCTGCGACCTTTCT
 K  D  V  L  Y  S  L  N  I  T  E  I  F  S  G  G  C  D  L  S
        1030              1050               1070
GGAATAACAGATTCATCTGAAGTGTATGTTTCCCAAGTGACGCAAAAAGTTTTCTTTGAG
 G  I  T  D  S  S  E  V  Y  V  S  Q  V  T  Q  K  V  F  F  E
        1090              1110               1130
ATAAATGAAGATGGTAGTGAAGCTGCAACATCAACTGGCATACACATCCCTGTGATCATG
 I  N  E  D  G  S  E  A  A  T  S  T  G  I  H  I  P  V  I  M
        1150              1170               1190
AGTCTGGCTCAAAGCCAATTTATAGCAAATCATCCATTTCTGTTTATTATGAAGCATAAT
 S  L  A  Q  S  Q  F  I  A  N  H  P  F  L  F  I  M  K  H  N
        1210              1230               1250
CCAACAGAATCAATTCTGTTTATGGGAAGAGTGACAAATCCCTGACACCCAGGAGATAAA
 P  T  E  S  I  L  F  M  G  R  V  T  N  P  *
        1270              1290               1310
AGGAAGAGATTTAGATTCACTGTGAATGAAAAGCACAGCCTCAGAATAAAAGATGATTTC
        1330              1350               1370
TCAAAAATAAAAAAAAAAAAAAAAAAAAAAAAAAAAAAAAAAAAAAAAAAAAAAAAAAAA
```

```
319 T Q M F R Q F Q A D F I S L S D Q E P L H V A Q A L Q K V K  PAI-1 M16006
330 E D A F N K C R A N F S G M E R N D F L S E V F H Q A M  PAI-2 M18082
308 T E I F S G - C D L S G I T D S S E V Y V S Q T Q K V F  HPASD50P protein 349 I E V N E S G T V A S S T A V I V S A R M - - A P E E I I  PAI-1 M16006
360 V D V N E E G T E A A A G T G G V M T G R T G H G G P Q F V  PAI-2 M18082
337 F E I N E D G S E A A T S G I - H I P V I M S L A Q S Q F I  HPASD50P protein 377 M D R P F L F V V R H N P T G T V L F M G Q V M E - P     PAI-1 M16006
390 A D H P F L F L I M H K I T N C I L F F G R F C S P     PAI-2 M18082
367 A N H P F L F M K H N P I E S I L F M G R V T N P     HPASD50P protein
```

Decoration 'Decortion #1': Box residues that match the Consensus exactly.

FIG.2C

```
GGCACGAGGG AAAACTCTAT TTTGAAAATG AATATATTTT GATTTAAACA ATACAGAGAA                    60
GTCAAA ATG GAC ACA ATC TTC TTG TGG AGT CTT CTA TTG CTG TTT TTT                      108
       Met Asp Thr Ile Phe Leu Trp Ser Leu Leu Leu Leu Phe Phe
GCA AGT CAA GCC TCA AGA TGC TCA GCT CAA AAA AAT ACC GAA TTT GCA                     156
Gly Ser Gln Ala Ser Arg Cys Ser Ala Gln Lys Asn Thr Glu Phe Ala
GTG GAT CTT TAT CAA GAG GTT TCC TTA TCT CAT AAG GAC AAC ATT ATA                     204
Val Asp Leu Tyr Gln Glu Val Ser Leu Ser His Lys Asp Asn Ile Ile
TTT TCA CCC CTT GGA ATA ACT TTG GTT CTT GAG ATG GTA CAA CTG GGA                     252
Phe Ser Pro Leu Gly Ile Thr Leu Val Leu Glu Met Val Gln Leu Gly
GCC AAA GGA AAA GCA CAG CAG CAG ATA AGA CAA ACT TTA AAA CAA CAG                     300
Ala Lys Gly Lys Ala Gln Gln Gln Ile Arg Gln Thr Leu Lys Gln Gln
GAA ACC TCA GCT GGG GAA GAA TTT TTG GTA CTG AAG TCA TTT TGC TCT                     348
Glu Thr Ser Ala Gly Glu Glu Phe Leu Val Leu Lys Ser Phe Cys Ser
GCC ATC TCA GAG AAA AAA CAA GAA TTT ACA TTT AAT CTT GCC AAT GCC                     396
Ala Ile Ser Glu Lys Lys Gln Glu Phe Thr Phe Asn Leu Ala Asn Ala
CTC TAC CTT CAA GAA GGA TTC ACT GTG AAA GAA CAG TAT CTC CAT GGC                     444
Leu Tyr Leu Gln Glu Gly Phe Thr Val Lys Glu Gln Tyr Leu His Gly
AAC AAG GAA TTT TTT CAG AGT GCT ATA AAA CTG GTG GAT TTT CAA GAT                     492
Asn Lys Glu Phe Phe Gln Ser Ala Ile Lys Leu Val Asp Phe Gln Asp
GCA AAG GCT TGT GCA GAG ATG ATA AGT ACC TGG GTA GAA AGA AAA ACA                     540
Ala Lys Ala Cys Ala Glu Met Ile Ser Thr Trp Val Glu Arg Lys Thr
GAT GGA AAA ATT AAA GAC ATG TTT TCA GGG GAA GAA TTT GGC CCT CTG                     588
Asp Gly Lys Ile Lys Asp Met Phe Ser Gly Glu Glu Phe Gly Pro Leu
ACT CGG CTT GTC CTG GTG AAT GCT ATT TAT TTC AAA GGA GAT TGG AAA                     636
Thr Arg Leu Val Leu Val Asn Ala Ile Tyr Phe Lys Gly Asp Trp Lys
CAG AAA TTC AGA AAA GAG GAC ACA CAG CTG ATA AAT TTT ACT AAG AAA                     684
Gln Lys Phe Arg Lys Glu Asp Thr Gln Leu Ile Asn Phe Thr Lys Lys
AAT GGT TCA ACT GTC AAA ATT CCA ATG ATG AAG GCT CTT CTG AGA ACA                     732
Asn Gly Ser Thr Val Lys Ile Pro Met Met Lys Ala Leu Leu Arg Thr
AAA TAT GGT TAT TTT TCT GAA TCT TCC CTG AAC TAC CAA GTT TTA GAA                     780
Lys Tyr Gly Tyr Phe Ser Glu Ser Ser Leu Asn Tyr Gln Val Leu Glu
TTG TCT TAC AAA GGT GAT GAA TTT AGC TTA ATT ATC ATA CTT CCT GCA                     828
Leu Ser Tyr Lys Gly Asp Glu Phe Ser Leu Ile Ile Ile Leu Pro Ala
GAA GGT ATG GAT ATA GAA GAA GTG GAA AAA CTA ATT ACT GCT CAA CAA                     876
Glu Gly Met Asp Ile Glu Glu Val Glu Lys Leu Ile Thr Ala Gln Gln
ATC CTA AAA TGG CTC TCT GAG ATG CAA GAA GAG GAA GTA GAA ATA AGC                     924
Ile Leu Lys Trp Leu Ser Glu Met Gln Glu Glu Glu Val Glu Ile Ser
CTC CCT AGA TTT AAA GTA GAA CAA AAA GTA GAC TTC AAA GAC GTT TTG                     972
Leu Pro Arg Phe Lys Val Glu Gln Lys Val Asp Phe Lys Asp Val Leu
TAT TCT TTG AAC ATA ACC GAG ATA TTT AGT GGT GGC TGC GAC CTT TCT                    1020
Tyr Ser Leu Asn Ile Thr Glu Ile Phe Ser Gly Gly Cys Asp Leu Ser
GCA ATA ACA GAT TCA TCT GAA GTG TAT GTT TCC CAA GTG ACG CAA AAA                    1068
Gly Ile Thr Asp Ser Ser Glu Val Tyr Val Ser Gln Val Thr Gln Lys
GTT TTC TTT GAG ATA AAT GAA GAT GGT AGT GAA GCT GCA ACA TCA ACT                    1116
Val Phe Phe Glu Ile Asn Glu Asp Gly Ser Glu Ala Ala Thr Ser Thr
GGC ATA CAC ATC CCT GTG ATC ATG AGT CTG GCT CAA AGC CAA TTT ATA                    1164
```

FIG.4A

```
Gly Ile His Ile Pro Val Ile Met Ser Leu Ala Gln Ser Gln Phe Ile
GCA AAT CAT CCA TTT CTG TTT ATT ATG AAG CAT AAT CCA ACA GAA TCA        1212
Ala Asn His Pro Phe Leu Phe Ile Met Lys His Asn Pro Thr Glu Ser
ATT CTG TTT ATG GGA AGA GTG ACA AAT CCT GAC ACC CAG GAG ATA AAA        1260
Ile Leu Phe Met Gly Arg Val Thr Asn Pro Asp Thr Gln Glu Ile Lys
GGA AGA GAT TTA GAT TCA CTG TGAATGAAAA GCACAGCCTC AGAATAAAAG           1311
Gly Arg Asp Leu Asp Ser Leu
ATGATTTCTC AAAAATAAAA AAAAAAAAAA AAAAAAAAAA AAAAAAAAAA AAAAAAAA        1370
```

FIG.4B

```
                       -35      OPERATOR1
1   AAGCTTAAAAAACTGCAAAAAATACTT TGACTT GTGAGCGGATAACAAT

OPERATOR2
50  TAAGAT CTACCCAA ATTGTGAGCGGATAACAA TTCACACATTAA
     -10

94  A CAGGAG AAATTA CATATG
    S/D
```

FIG. 6

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 1371 base pairs
      (B) TYPE: nucleic acid
      (C) STRANDEDNESS: double
      (D) TOPOLOGY: both (ii) MOLECULE TYPE: cDNA (ix) FEATURE:
      (A) NAME/KEY: CDS
      (B) LOCATION: 67..1242

(ix) FEATURE:
      (A) NAME/KEY: mat_peptide
      (B) LOCATION: 109..1242

(ix) FEATURE:
      (A) NAME/KEY: sig_peptide
      (B) LOCATION: 67..108

(xi) SEQUENCE DESCRIPTION: SEQ ID NO: 1:

```
GGCACGAGGG AAAACTCTAT TTTGAAAATG AATATATTTT GATTTAAACA ATACAGAGAA         60

GTCAAA ATG GAC ACA ATC TTC TTG TGG AGT CTT CTA TTG CTG TTT TTT          108
       Met Asp Thr Ile Phe Leu Trp Ser Leu Leu Leu Leu Phe Phe
        -14              -10                  -5

GGA AGT CAA GCC TCA AGA TGC TCA GCT CAA AAA AAT ACC GAA TTT GCA         156
Gly Ser Gln Ala Ser Arg Cys Ser Ala Gln Lys Asn Thr Glu Phe Ala
 1               5                  10                  15

GTG GAT CTT TAT CAA GAG GTT TCC TTA TCT CAT AAG GAC AAC ATT ATA         204
Val Asp Leu Tyr Gln Glu Val Ser Leu Ser His Lys Asp Asn Ile Ile
             20                  25                  30

TTT TCA CCC CTT GGA ATA ACT TTG GTT CTT GAG ATG GTA CAA CTG GGA         252
Phe Ser Pro Leu Gly Ile Thr Leu Val Leu Glu Met Val Gln Leu Gly
         35                  40                  45

GCC AAA GGA AAA GCA CAG CAG CAG ATA AGA CAA ACT TTA AAA CAA CAG         300
Ala Lys Gly Lys Ala Gln Gln Gln Ile Arg Gln Thr Leu Lys Gln Gln
 50                  55                  60

GAA ACC TCA GCT GGG GAA GAA TTT TTG GTA CTG AAG TCA TTT TGC TCT         348
Glu Thr Ser Ala Gly Glu Glu Phe Leu Val Leu Lys Ser Phe Cys Ser
 65                  70                  75                  80

GCC ATC TCA GAG AAA AAA CAA GAA TTT ACA TTT AAT CTT GCC AAT GCC         396
Ala Ile Ser Glu Lys Lys Gln Glu Phe Thr Phe Asn Leu Ala Asn Ala
                 85                  90                  95

CTC TAC CTT CAA GAA GGA TTC ACT GTG AAA GAA CAG TAT CTC CAT GGC         444
Leu Tyr Leu Gln Glu Gly Phe Thr Val Lys Glu Gln Tyr Leu His Gly
                100                 105                 110

AAC AAG GAA TTT TTT CAG AGT GCT ATA AAA CTG GTG GAT TTT CAA GAT         492
Asn Lys Glu Phe Phe Gln Ser Ala Ile Lys Leu Val Asp Phe Gln Asp
            115                 120                 125

GCA AAG GCT TGT GCA GAG ATG ATA AGT ACC TGG GTA GAA AGA AAA ACA         540
Ala Lys Ala Cys Ala Glu Met Ile Ser Thr Trp Val Glu Arg Lys Thr
130                 135                 140

GAT GGA AAA ATT AAA GAC ATG TTT TCA GGG GAA GAA TTT GGC CCT CTG         588
Asp Gly Lys Ile Lys Asp Met Phe Ser Gly Glu Glu Phe Gly Pro Leu
145                 150                 155                 160

ACT CGG CTT GTC CTG GTG AAT GCT ATT TAT TTC AAA GGA GAT TGG AAA         636
```

-continued

```
Thr Arg Leu Val Leu Val Asn Ala Ile Tyr Phe Lys Gly Asp Trp Lys
            165                 170                 175

CAG AAA TTC AGA AAA GAG GAC ACA CAG CTG ATA AAT TTT ACT AAG AAA       684
Gln Lys Phe Arg Lys Glu Asp Thr Gln Leu Ile Asn Phe Thr Lys Lys
                180                 185                 190

AAT GGT TCA ACT GTC AAA ATT CCA ATG ATG AAG GCT CTT CTG AGA ACA       732
Asn Gly Ser Thr Val Lys Ile Pro Met Met Lys Ala Leu Leu Arg Thr
                195                 200                 205

AAA TAT GGT TAT TTT TCT GAA TCT TCC CTG AAC TAC CAA GTT TTA GAA       780
Lys Tyr Gly Tyr Phe Ser Glu Ser Ser Leu Asn Tyr Gln Val Leu Glu
        210                 215                 220

TTG TCT TAC AAA GGT GAT GAA TTT AGC TTA ATT ATC ATA CTT CCT GCA       828
Leu Ser Tyr Lys Gly Asp Glu Phe Ser Leu Ile Ile Ile Leu Pro Ala
225                 230                 235                 240

GAA GGT ATG GAT ATA GAA GAA GTG GAA AAA CTA ATT ACT GCT CAA CAA       876
Glu Gly Met Asp Ile Glu Glu Val Glu Lys Leu Ile Thr Ala Gln Gln
                245                 250                 255

ATC CTA AAA TGG CTC TCT GAG ATG CAA GAA GAG GAA GTA GAA ATA AGC       924
Ile Leu Lys Trp Leu Ser Glu Met Gln Glu Glu Glu Val Glu Ile Ser
                260                 265                 270

CTC CCT AGA TTT AAA GTA GAA CAA AAA GTA GAC TTC AAA GAC GTT TTG       972
Leu Pro Arg Phe Lys Val Glu Gln Lys Val Asp Phe Lys Asp Val Leu
        275                 280                 285

TAT TCT TTG AAC ATA ACC GAG ATA TTT AGT GGT GGC TGC GAC CTT TCT      1020
Tyr Ser Leu Asn Ile Thr Glu Ile Phe Ser Gly Gly Cys Asp Leu Ser
        290                 295                 300

GGA ATA ACA GAT TCA TCT GAA GTG TAT GTT TCC CAA GTG ACG CAA AAA      1068
Gly Ile Thr Asp Ser Ser Glu Val Tyr Val Ser Gln Val Thr Gln Lys
305                 310                 315                 320

GTT TTC TTT GAG ATA AAT GAA GAT GGT AGT GAA GCT GCA ACA TCA ACT      1116
Val Phe Phe Glu Ile Asn Glu Asp Gly Ser Glu Ala Ala Thr Ser Thr
                325                 330                 335

GGC ATA CAC ATC CCT GTG ATC ATG AGT CTG GCT CAA AGC CAA TTT ATA      1164
Gly Ile His Ile Pro Val Ile Met Ser Leu Ala Gln Ser Gln Phe Ile
                340                 345                 350

GCA AAT CAT CCA TTT CTG TTT ATT ATG AAG CAT AAT CCA ACA GAA TCA      1212
Ala Asn His Pro Phe Leu Phe Ile Met Lys His Asn Pro Thr Glu Ser
        355                 360                 365

ATT CTG TTT ATG GGA AGA GTG ACA AAT CCC TGACACCCAG GAGATAAAAG        1262
Ile Leu Phe Met Gly Arg Val Thr Asn Pro
        370                 375

GAAGAGATTT AGATTCACTG TGAATGAAAA GCACAGCCTC AGAATAAAAG ATGATTTCTC    1322

AAAAATAAAA AAAAAAAAAA AAAAAAAAAA AAAAAAAAAA AAAAAAAA                1371

(2) INFORMATION FOR SEQ ID NO: 2:

(i) SEQUENCE CHARACTERISTICS:
        (A) LENGTH: 392 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Thr Ile Phe Leu Trp Ser Leu Leu Leu Leu Phe Phe Gly Ser
-14                 -10                 -5                  1

Gln Ala Ser Arg Cys Ser Ala Gln Lys Asn Thr Glu Phe Ala Val Asp
            5                   10                  15

Leu Tyr Gln Glu Val Ser Leu Ser His Lys Asp Asn Ile Ile Phe Ser
        20                  25                  30
```

Pro Leu Gly Ile Thr Leu Val Leu Glu Met Val Gln Leu Gly Ala Lys
35                  40                  45                  50

Gly Lys Ala Gln Gln Ile Arg Gln Thr Leu Lys Gln Gln Glu Thr
            55                  60                  65

Ser Ala Gly Glu Glu Phe Leu Val Leu Lys Ser Phe Cys Ser Ala Ile
            70                  75                  80

Ser Glu Lys Lys Gln Glu Phe Thr Phe Asn Leu Ala Asn Ala Leu Tyr
            85                  90                  95

Leu Gln Glu Gly Phe Thr Val Lys Glu Gln Tyr Leu His Gly Asn Lys
            100                 105                 110

Glu Phe Phe Gln Ser Ala Ile Lys Leu Val Asp Phe Gln Asp Ala Lys
115                 120                 125                 130

Ala Cys Ala Glu Met Ile Ser Thr Trp Val Glu Arg Lys Thr Asp Gly
                135                 140                 145

Lys Ile Lys Asp Met Phe Ser Gly Glu Glu Phe Gly Pro Leu Thr Arg
                150                 155                 160

Leu Val Leu Val Asn Ala Ile Tyr Phe Lys Gly Asp Trp Lys Gln Lys
                165                 170                 175

Phe Arg Lys Glu Asp Thr Gln Leu Ile Asn Phe Thr Lys Lys Asn Gly
180                 185                 190

Ser Thr Val Lys Ile Pro Met Met Lys Ala Leu Leu Arg Thr Lys Tyr
195                 200                 205                 210

Gly Tyr Phe Ser Glu Ser Ser Leu Asn Tyr Gln Val Leu Glu Leu Ser
            215                 220                 225

Tyr Lys Gly Asp Glu Phe Ser Leu Ile Ile Leu Pro Ala Glu Gly
            230                 235                 240

Met Asp Ile Glu Glu Val Glu Lys Leu Ile Thr Ala Gln Gln Ile Leu
            245                 250                 255

Lys Trp Leu Ser Glu Met Gln Glu Glu Val Glu Ile Ser Leu Pro
260                 265                 270

Arg Phe Lys Val Glu Gln Lys Val Asp Phe Lys Asp Val Leu Tyr Ser
275                 280                 285                 290

Leu Asn Ile Thr Glu Ile Phe Ser Gly Gly Cys Asp Leu Ser Gly Ile
                295                 300                 305

Thr Asp Ser Ser Glu Val Tyr Val Ser Gln Val Thr Gln Lys Val Phe
            310                 315                 320

Phe Glu Ile Asn Glu Asp Gly Ser Glu Ala Ala Thr Ser Thr Gly Ile
            325                 330                 335

His Ile Pro Val Ile Met Ser Leu Ala Gln Ser Gln Phe Ile Ala Asn
340                 345                 350

His Pro Phe Leu Phe Ile Met Lys His Asn Pro Thr Glu Ser Ile Leu
355                 360                 365                 370

Phe Met Gly Arg Val Thr Asn Pro
                375

(2) INFORMATION FOR SEQ ID NO: 3:

(i) SEQUENCE CHARACTERISTICS:
        (A) LENGTH: 402 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

-continued

```
Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
            20                  25                  30

His Leu Ala Ser Asp Phe Gly Val Arg Val Phe Gln Gln Val Ala Gln
            35                  40                  45

Ala Ser Lys Asp Arg Asn Val Val Phe Ser Pro Tyr Gly Val Ala Ser
        50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
            115                 120                 125

Val Gln Gly Phe Met Pro His Phe Phe Arg Leu Phe Arg Ser Thr Val
130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
            195                 200                 205

Arg Arg Leu Phe His Lys Ser Asp Gly Ser Thr Val Ser Val Pro Met
210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
            275                 280                 285

Met Thr Arg Leu Pro Arg Leu Leu Val Leu Pro Lys Phe Ser Leu Glu
290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Thr Ala Val Ile Val Ser Ala
            355                 360                 365

Arg Met Ala Pro Glu Glu Ile Ile Met Asp Arg Pro Phe Leu Phe Val
370                 375                 380

Val Arg His Asn Pro Thr Gly Thr Val Leu Phe Met Gly Gln Val Met
385                 390                 395                 400

Glu Pro
```

(2) INFORMATION FOR SEQ ID NO: 4:

(i) SEQUENCE CHARACTERISTICS:
        (A) LENGTH: 415 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Glu Asp Leu Cys Val Ala Asn Thr Leu Phe Ala Leu Asn Leu Phe
  1               5                  10                  15

Lys His Leu Ala Lys Ala Ser Pro Thr Gln Asn Leu Phe Leu Ser Pro
                 20                  25                  30

Trp Ser Ile Ser Ser Thr Met Ala Met Val Tyr Met Gly Ser Arg Gly
             35                  40                  45

Ser Thr Glu Asp Gln Met Ala Lys Val Leu Gln Phe Asn Glu Val Gly
         50                  55                  60

Ala Asn Ala Val Thr Pro Met Thr Pro Glu Asn Phe Thr Ser Cys Gly
 65                  70                  75                  80

Phe Met Gln Gln Ile Gln Lys Gly Ser Tyr Pro Asp Ala Ile Leu Gln
                 85                  90                  95

Ala Gln Ala Ala Asp Lys Ile His Ser Ser Phe Arg Ser Leu Ser Ser
            100                 105                 110

Ala Ile Asn Ala Ser Thr Gly Asp Tyr Leu Leu Glu Ser Val Asn Lys
        115                 120                 125

Leu Phe Gly Glu Lys Ser Ala Ser Phe Arg Glu Glu Tyr Ile Arg Leu
    130                 135                 140

Cys Gln Lys Tyr Tyr Ser Ser Glu Pro Gln Ala Val Asp Phe Leu Glu
145                 150                 155                 160

Cys Ala Glu Glu Ala Arg Lys Lys Ile Asn Ser Trp Val Lys Thr Gln
                165                 170                 175

Thr Lys Gly Lys Ile Pro Asn Leu Leu Pro Glu Gly Ser Val Asp Gly
            180                 185                 190

Asp Thr Arg Met Val Leu Val Asn Ala Val Tyr Phe Lys Gly Lys Trp
        195                 200                 205

Lys Thr Pro Phe Glu Lys Lys Leu Asn Gly Leu Tyr Pro Phe Arg Val
    210                 215                 220

Asn Ser Ala Gln Arg Thr Pro Val Gln Met Met Tyr Leu Arg Glu Lys
225                 230                 235                 240

Leu Asn Ile Gly Tyr Ile Glu Asp Leu Lys Ala Gln Ile Leu Glu Leu
                245                 250                 255

Pro Tyr Ala Gly Asp Val Ser Met Phe Leu Leu Leu Pro Asp Glu Ile
            260                 265                 270

Ala Asp Val Ser Thr Gly Leu Glu Leu Leu Glu Ser Glu Ile Thr Tyr
        275                 280                 285

Asp Lys Leu Asn Lys Trp Thr Ser Lys Asp Lys Met Ala Glu Asp Glu
    290                 295                 300

Val Glu Val Tyr Ile Pro Gln Phe Lys Leu Glu Glu His Tyr Glu Leu
305                 310                 315                 320

Arg Ser Ile Leu Arg Ser Met Gly Met Glu Asp Ala Phe Asn Lys Gly
                325                 330                 335

Arg Ala Asn Phe Ser Gly Met Ser Glu Arg Asn Asp Leu Phe Leu Ser
            340                 345                 350

Glu Val Phe His Gln Ala Met Val Asp Val Asn Glu Glu Gly Thr Glu
```

```
            355                 360                 365
Ala Ala Ala Gly Thr Gly Gly Val Met Thr Gly Arg Thr Gly His Gly
    370                 375                 380

Gly Pro Gln Phe Val Ala Asp His Pro Phe Leu Phe Leu Ile Met His
385                 390                 395                 400

Lys Ile Thr Lys Cys Ile Leu Phe Phe Gly Arg Phe Cys Ser Pro
                405                 410                 415
```

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

CGCCCATGGG AAGTCAAGCC TCAAG                                      25

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CGCAAGCTTT CACTTCCTTT TATCTCCCTG                             30

(2) INFORMATION FOR SEQ ID NO: 7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

CGCGGATCCG CCATCATGGA CACAATCTTC TTG                        33

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CGCGGTACCT CACTTCCTTT TATCTCCCTG                             30

(2) INFORMATION FOR SEQ ID NO: 9:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

CGCTCTAGAT CAAGCGTAGT CTGGGACGTC GTATGGGTAG GGATTTGTCA CTCTTCC       57

(2) INFORMATION FOR SEQ ID NO: 10:

(i) SEQUENCE CHARACTERISTICS:
            (A) LENGTH: 171 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 10:

NAATATATTT NNATTTAAAC AATACAGAGA AGTCAAAATG GACACAATCT TCTTGTGGAG      60

TCTTCTATTG CTGTTTTTTC GAAGTCAAGC CTCANGAATG CTCAGCTGCA AAAAAATACC    120

GAATTTGCCA GTGGNATCTT TATCAAGAGG TTTCCTTCAT CTGCATAAGG N             171

(2) INFORMATION FOR SEQ ID NO: 11:

(i) SEQUENCE CHARACTERISTICS:
            (A) LENGTH: 515 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 11:

GGCANNANAA CAATCTNATC CAAGGACTGT GGNACTCCTG TTCCCTGCTC ATCATGTCAT     60

GGGGCATCTG CCAGGAACCA TCTTTGATGG TGTAAAAATC TTGAATACAT AAGAGGGAAA   120

TTTTAGACTT GTTAGAAAGA AGCCAAGCAA TTGAGACCTT AGATAGAACT TAGAATTCTC   180

GCCGAGTTTT GTTGGGTAAT TGTTACTTCA AAAAAAAATG CAATTTCTGT TCCCTCTTTC   240

CTCCAACCAT TTATCTGGGA AGCAAGTTAT TGGCAACCCA GAGCTGATTG TTGGAGCCGG   300

GGAAAATGGT GTGAAATGTG AGAAAATGTA ATTGAGATAA TAAAAACAAA AGATTTTACA   360

ATATATTATC CTCTAAGTCA TCCATTAAAA AATTGGTAGC AAAAATGTGC AGTGTTTCAA   420

GACTTTTCTT TTCTTTTTTT TTNAATACCA GATTAAAGTA GACCAAAAAG TAGACTCCAA   480

AGACGTTTGG ATNCTTGAAC ATAACCGNGA TATTA                              515

(2) INFORMATION FOR SEQ ID NO: 12:

(i) SEQUENCE CHARACTERISTICS:
            (A) LENGTH: 1370 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 67..1281

(ix) FEATURE:
            (A) NAME/KEY: sig_peptide
            (B) LOCATION: 67..120

(ix) FEATURE:
            (A) NAME/KEY: mat_peptide
            (B) LOCATION: 121..1281

(xi) SEQUENCE DESCRIPTION: SEQ ID NO: 12:

```
GGCACGAGGG AAAACTCTAT TTTGAAAATG AATATATTTT GATTTAAACA ATACAGAGAA            60

GTCAAA ATG GAC ACA ATC TTC TTG TGG AGT CTT CTA TTG CTG TTT TTT             108
       Met Asp Thr Ile Phe Leu Trp Ser Leu Leu Leu Leu Phe Phe
       -18             -15             -10                  -5

GGA AGT CAA GCC TCA AGA TGC TCA GCT CAA AAA AAT ACC GAA TTT GCA            156
Gly Ser Gln Ala Ser Arg Cys Ser Ala Gln Lys Asn Thr Glu Phe Ala
            1               5                   10

GTG GAT CTT TAT CAA GAG GTT TCC TTA TCT CAT AAG GAC AAC ATT ATA            204
Val Asp Leu Tyr Gln Glu Val Ser Leu Ser His Lys Asp Asn Ile Ile
        15                  20                  25

TTT TCA CCC CTT GGA ATA ACT TTG GTT CTT GAG ATG GTA CAA CTG GGA            252
Phe Ser Pro Leu Gly Ile Thr Leu Val Leu Glu Met Val Gln Leu Gly
    30                  35                  40

GCC AAA GGA AAA GCA CAG CAG CAG ATA AGA CAA ACT TTA AAA CAA CAG            300
Ala Lys Gly Lys Ala Gln Gln Gln Ile Arg Gln Thr Leu Lys Gln Gln
45                  50                  55                  60

GAA ACC TCA GCT GGG GAA GAA TTT TTG GTA CTG AAG TCA TTT TGC TCT            348
Glu Thr Ser Ala Gly Glu Glu Phe Leu Val Leu Lys Ser Phe Cys Ser
                65                  70                  75

GCC ATC TCA GAG AAA AAA CAA GAA TTT ACA TTT AAT CTT GCC AAT GCC            396
Ala Ile Ser Glu Lys Lys Gln Glu Phe Thr Phe Asn Leu Ala Asn Ala
            80                  85                  90

CTC TAC CTT CAA GAA GGA TTC ACT GTG AAA GAA CAG TAT CTC CAT GGC            444
Leu Tyr Leu Gln Glu Gly Phe Thr Val Lys Glu Gln Tyr Leu His Gly
        95                  100                 105

AAC AAG GAA TTT TTT CAG AGT GCT ATA AAA CTG GTG GAT TTT CAA GAT            492
Asn Lys Glu Phe Phe Gln Ser Ala Ile Lys Leu Val Asp Phe Gln Asp
110                 115                 120

GCA AAG GCT TGT GCA GAG ATG ATA AGT ACC TGG GTA GAA AGA AAA ACA            540
Ala Lys Ala Cys Ala Glu Met Ile Ser Thr Trp Val Glu Arg Lys Thr
125                 130                 135                 140

GAT GGA AAA ATT AAA GAC ATG TTT TCA GGG GAA GAA TTT GGC CCT CTG            588
Asp Gly Lys Ile Lys Asp Met Phe Ser Gly Glu Glu Phe Gly Pro Leu
                145                 150                 155

ACT CGG CTT GTC CTG GTG AAT GCT ATT TAT TTC AAA GGA GAT TGG AAA            636
Thr Arg Leu Val Leu Val Asn Ala Ile Tyr Phe Lys Gly Asp Trp Lys
            160                 165                 170

CAG AAA TTC AGA AAA GAG GAC ACA CAG CTG ATA AAT TTT ACT AAG AAA            684
Gln Lys Phe Arg Lys Glu Asp Thr Gln Leu Ile Asn Phe Thr Lys Lys
        175                 180                 185

AAT GGT TCA ACT GTC AAA ATT CCA ATG ATG AAG GCT CTT CTG AGA ACA            732
Asn Gly Ser Thr Val Lys Ile Pro Met Met Lys Ala Leu Leu Arg Thr
190                 195                 200

AAA TAT GGT TAT TTT TCT GAA TCT TCC CTG AAC TAC CAA GTT TTA GAA            780
Lys Tyr Gly Tyr Phe Ser Glu Ser Ser Leu Asn Tyr Gln Val Leu Glu
205                 210                 215                 220

TTG TCT TAC AAA GGT GAT GAA TTT AGC TTA ATT ATC ATA CTT CCT GCA            828
Leu Ser Tyr Lys Gly Asp Glu Phe Ser Leu Ile Ile Ile Leu Pro Ala
                225                 230                 235

GAA GGT ATG GAT ATA GAA GAA GTG GAA AAA CTA ATT ACT GCT CAA CAA            876
Glu Gly Met Asp Ile Glu Glu Val Glu Lys Leu Ile Thr Ala Gln Gln
            240                 245                 250

ATC CTA AAA TGG CTC TCT GAG ATG CAA GAA GAG GAA GTA GAA ATA AGC            924
Ile Leu Lys Trp Leu Ser Glu Met Gln Glu Glu Glu Val Glu Ile Ser
        255                 260                 265

CTC CCT AGA TTT AAA GTA GAA CAA AAA GTA GAC TTC AAA GAC GTT TTG            972
Leu Pro Arg Phe Lys Val Glu Gln Lys Val Asp Phe Lys Asp Val Leu
```

-continued

```
                    270                 275                 280
TAT TCT TTG AAC ATA ACC GAG ATA TTT AGT GGT GGC TGC GAC CTT TCT     1020
Tyr Ser Leu Asn Ile Thr Glu Ile Phe Ser Gly Gly Cys Asp Leu Ser
285                 290                 295                 300

GGA ATA ACA GAT TCA TCT GAA GTG TAT GTT TCC CAA GTG ACG CAA AAA     1068
Gly Ile Thr Asp Ser Ser Glu Val Tyr Val Ser Gln Val Thr Gln Lys
                305                 310                 315

GTT TTC TTT GAG ATA AAT GAA GAT GGT AGT GAA GCT GCA ACA TCA ACT     1116
Val Phe Phe Glu Ile Asn Glu Asp Gly Ser Glu Ala Ala Thr Ser Thr
                320                 325                 330

GGC ATA CAC ATC CCT GTG ATC ATG AGT CTG GCT CAA AGC CAA TTT ATA     1164
Gly Ile His Ile Pro Val Ile Met Ser Leu Ala Gln Ser Gln Phe Ile
                335                 340                 345

GCA AAT CAT CCA TTT CTG TTT ATT ATG AAG CAT AAT CCA ACA GAA TCA     1212
Ala Asn His Pro Phe Leu Phe Ile Met Lys His Asn Pro Thr Glu Ser
350                 355                 360

ATT CTG TTT ATG GGA AGA GTG ACA AAT CCT GAC ACC CAG GAG ATA AAA     1260
Ile Leu Phe Met Gly Arg Val Thr Asn Pro Asp Thr Gln Glu Ile Lys
365                 370                 375                 380

GGA AGA GAT TTA GAT TCA CTG TGAATGAAAA GCACAGCCTC AGAATAAAAG        1311
Gly Arg Asp Leu Asp Ser Leu
                385

ATGATTTCTC AAAAATAAAA AAAAAAAAAA AAAAAAAAAA AAAAAAAAAA AAAAAAAA    1370
```

(2) INFORMATION FOR SEQ ID NO: 13:

(i) SEQUENCE CHARACTERISTICS:
        (A) LENGTH: 405 amino acids
        (B) TYPE: amino acid
        (D) TOPOLOGY: linear (ii) MOLECULE TYPE: protein (xi) SEQUENCE DESCRIPTION: SEQ ID NO: 13:

```
Met Asp Thr Ile Phe Leu Trp Ser Leu Leu Leu Phe Phe Gly Ser
-18             -15                 -10                 -5

Gln Ala Ser Arg Cys Ser Ala Gln Lys Asn Thr Glu Phe Ala Val Asp
                1               5                   10

Leu Tyr Gln Glu Val Ser Leu Ser His Lys Asp Asn Ile Ile Phe Ser
15                  20                  25                  30

Pro Leu Gly Ile Thr Leu Val Leu Glu Met Val Gln Leu Gly Ala Lys
                35                  40                  45

Gly Lys Ala Gln Gln Gln Ile Arg Gln Thr Leu Lys Gln Gln Glu Thr
                50                  55                  60

Ser Ala Gly Glu Glu Phe Leu Val Leu Lys Ser Phe Cys Ser Ala Ile
                65                  70                  75

Ser Glu Lys Lys Gln Glu Phe Thr Phe Asn Leu Ala Asn Ala Leu Tyr
80                  85                  90

Leu Gln Glu Gly Phe Thr Val Lys Glu Gln Tyr Leu His Gly Asn Lys
95                  100                 105                 110

Glu Phe Phe Gln Ser Ala Ile Lys Leu Val Asp Phe Gln Asp Ala Lys
                115                 120                 125

Ala Cys Ala Glu Met Ile Ser Thr Trp Val Glu Arg Lys Thr Asp Gly
                130                 135                 140

Lys Ile Lys Asp Met Phe Ser Gly Glu Glu Phe Gly Pro Leu Thr Arg
                145                 150                 155

Leu Val Leu Val Asn Ala Ile Tyr Phe Lys Gly Asp Trp Lys Gln Lys
160                 165                 170
```

```
Phe Arg Lys Glu Asp Thr Gln Leu Ile Asn Phe Thr Lys Lys Asn Gly
175                 180                 185                 190

Ser Thr Val Lys Ile Pro Met Met Lys Ala Leu Leu Arg Thr Lys Tyr
            195                 200                 205

Gly Tyr Phe Ser Glu Ser Ser Leu Asn Tyr Gln Val Leu Glu Leu Ser
                210                 215                 220

Tyr Lys Gly Asp Glu Phe Ser Leu Ile Ile Ile Leu Pro Ala Glu Gly
            225                 230                 235

Met Asp Ile Glu Glu Val Glu Lys Leu Ile Thr Ala Gln Gln Ile Leu
240                 245                 250

Lys Trp Leu Ser Glu Met Gln Glu Glu Val Glu Ile Ser Leu Pro
255                 260                 265                 270

Arg Phe Lys Val Glu Gln Lys Val Asp Phe Lys Asp Val Leu Tyr Ser
                275                 280                 285

Leu Asn Ile Thr Glu Ile Phe Ser Gly Gly Cys Asp Leu Ser Gly Ile
            290                 295                 300

Thr Asp Ser Ser Glu Val Tyr Val Ser Gln Val Thr Gln Lys Val Phe
            305                 310                 315

Phe Glu Ile Asn Glu Asp Gly Ser Glu Ala Ala Thr Ser Thr Gly Ile
320                 325                 330

His Ile Pro Val Ile Met Ser Leu Ala Gln Ser Gln Phe Ile Ala Asn
335                 340                 345                 350

His Pro Phe Leu Phe Ile Met Lys His Asn Pro Thr Glu Ser Ile Leu
                355                 360                 365

Phe Met Gly Arg Val Thr Asn Pro Asp Thr Gln Glu Ile Lys Gly Arg
            370                 375                 380

Asp Leu Asp Ser Leu
            385

(2) INFORMATION FOR SEQ ID NO: 14:

(i) SEQUENCE CHARACTERISTICS:
        (A) LENGTH: 3974 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 14:

GGTACCTAAG TGAGTAGGGC GTCCGATCGA CGGACGCCTT TTTTTTGAAT TCGTAATCAT     60

GGTCATAGCT GTTTCCTGTG TGAAATTGTT ATCCGCTCAC AATTCCACAC AACATACGAG    120

CCGGAAGCAT AAAGTGTAAA GCCTGGGGTG CCTAATGAGT GAGCTAACTC ACATTAATTG    180

CGTTGCGCTC ACTGCCCGCT TTCCAGTCGG GAAACCTGTC GTGCCAGCTG CATTAATGAA    240

TCGGCCAACG CGCGGGGAGA GGCGGTTTGC GTATTGGGCG CTCTTCCGCT TCCTCGCTCA    300

CTGACTCGCT GCGCTCGGTC GTTCGGCTGC GGCGAGCGGT ATCAGCTCAC TCAAAGGCGG    360

TAATACGGTT ATCCACAGAA TCAGGGGATA ACGCAGGAAA GAACATGTGA GCAAAAGGCC    420

AGCAAAAGGC CAGGAACCGT AAAAAGGCCG CGTTGCTGGC GTTTTTCCAT AGGCTCCGCC    480

CCCCTGACGA GCATCACAAA AATCGACGCT CAAGTCAGAG GTGGCGAAAC CCGACAGGAC    540

TATAAAGATA CCAGGCGTTT CCCCCTGGAA GCTCCCTCGT GCGCTCTCCT GTTCCGACCC    600

TGCCGCTTAC CGGATACCTG TCCGCCTTTC TCCCTTCGGG AAGCGTGGCG CTTTCTCATA    660

GCTCACGCTG TAGGTATCTC AGTTCGGTGT AGGTCGTTCG CTCCAAGCTG GGCTGTGTGC    720
```

```
ACGAACCCCC CGTTCAGCCC GACCGCTGCG CCTTATCCGG TAACTATCGT CTTGAGTCCA      780
ACCCGGTAAG ACACGACTTA TCGCCACTGG CAGCAGCCAC TGGTAACAGG ATTAGCAGAG      840
CGAGGTATGT AGGCGGTGCT ACAGAGTTCT TGAAGTGGTG GCCTAACTAC GGCTACACTA      900
GAAGAACAGT ATTTGGTATC TGCGCTCTGC TGAAGCCAGT TACCTTCGGA AAAAGAGTTG      960
GTAGCTCTTG ATCCGGCAAA CAAACCACCG CTGGTAGCGG TGGTTTTTTT GTTTGCAAGC     1020
AGCAGATTAC GCGCAGAAAA AAAGGATCTC AAGAAGATCC TTTGATCTTT TCTACGGGGT     1080
CTGACGCTCA GTGGAACGAA AACTCACGTT AAGGGATTTT GGTCATGAGA TTATCGTCGA     1140
CAATTCGCGC GCGAAGGCGA AGCGGCATGC ATTTACGTTG ACACCATCGA ATGGTGCAAA     1200
ACCTTTCGCG GTATGGCATG ATAGCGCCCG GAAGAGAGTC AATTCAGGGT GGTGAATGTG     1260
AAACCAGTAA CGTTATACGA TGTCGCAGAG TATGCCGGTG TCTCTTATCA GACCGTTTCC     1320
CGCGTGGTGA ACCAGGCCAG CCACGTTTCT GCGAAAACGC GGGAAAAAGT GGAAGCGGCG     1380
ATGGCGGAGC TGAATTACAT TCCCAACCGC GTGGCACAAC AACTGGCGGG CAAACAGTCG     1440
TTGCTGATTG GCGTTGCCAC CTCCAGTCTG GCCCTGCACG CGCCGTCGCA AATTGTCGCG     1500
GCGATTAAAT CTCGCGCCGA TCAACTGGGT GCCAGCGTGG TGGTGTCGAT GGTAGAACGA     1560
AGCGGCGTCG AAGCCTGTAA AGCGGCGGTG CACAATCTTC TCGCGCAACG CGTCAGTGGG     1620
CTGATCATTA ACTATCCGCT GGATGACCAG GATGCCATTG CTGTGGAAGC TGCCTGCACT     1680
AATGTTCCGG CGTTATTTCT TGATGTCTCT GACCAGACAC CCATCAACAG TATTATTTTC     1740
TCCCATGAAG ACGGTACGCG ACTGGGCGTG GAGCATCTGG TCGCATTGGG TCACCAGCAA     1800
ATCGCGCTGT TAGCGGGCCC ATTAAGTTCT GTCTCGGCGC GTCTGCGTCT GGCTGGCTGG     1860
CATAAATATC TCACTCGCAA TCAAATTCAG CCGATAGCGG AACGGGAAGG CGACTGGAGT     1920
GCCATGTCCG GTTTTCAACA AACCATGCAA ATGCTGAATG AGGGCATCGT TCCCACTGCG     1980
ATGCTGGTTG CCAACGATCA GATGGCGCTG GGCGCAATGC GCGCCATTAC CGAGTCCGGG     2040
CTGCGCGTTG GTGCGGATAT CTCGGTAGTG GGATACGACG ATACCGAAGA CAGCTCATGT     2100
TATATCCCGC CGTTAACCAC CATCAAACAG GATTTTCGCC TGCTGGGGCA AACCAGCGTG     2160
GACCGCTTGC TGCAACTCTC TCAGGGCCAG GCGGTGAAGG GCAATCAGCT GTTGCCCGTC     2220
TCACTGGTGA AAAGAAAAAC CACCCTGGCG CCCAATACGC AAACCGCCTC TCCCCGCGCG     2280
TTGGCCGATT CATTAATGCA GCTGGCACGA CAGGTTTCCC GACTGGAAAG CGGGCAGTGA     2340
GCGCAACGCA ATTAATGTAA GTTAGCGCGA ATTGTCGACC AAAGCGGCCA TCGTGCCTCC     2400
CCACTCCTGC AGTTCGGGGG CATGGATGCG CGGATAGCCG CTGCTGGTTT CCTGGATGCC     2460
GACGGATTTG CACTGCCGGT AGAACTCCGC GAGGTCGTCC AGCCTCAGGC AGCAGCTGAA     2520
CCAACTCGCG AGGGGATCGA GCCCGGGGTG GGCGAAGAAC TCCAGCATGA GATCCCCGCG     2580
CTGGAGGATC ATCCAGCCGG CGTCCCGGAA AACGATTCCG AAGCCCAACC TTTCATAGAA     2640
GGCGGCGGTG GAATCGAAAT CTCGTGATGG CAGGTTGGGC GTCGCTTGGT CGGTCATTTC     2700
GAACCCCAGA GTCCCGCTCA GAAGAACTCG TCAAGAAGGC GATAGAAGGC GATGCGCTGC     2760
GAATCGGGAG CGGCGATACC GTAAAGCACG AGGAAGCGGT CAGCCCATTC GCCGCCAAGC     2820
TCTTCAGCAA TATCACGGGT AGCCAACGCT ATGTCCTGAT AGCGGTCCGC CACACCCAGC     2880
CGGCCACAGT CGATGAATCC AGAAAAGCGG CCATTTTCCA CCATGATATT CGGCAAGCAG     2940
GCATCGCCAT GGGTCACGAC GAGATCCTCG CCGTCGGGCA TGCGCGCCTT GAGCCTGGCG     3000
AACAGTTCGG CTGGCGCGAG CCCCTGATGC TCTTCGTCCA GATCATCCTG ATCGACAAGA     3060
```

-continued

| | | | | | |
|---|---|---|---|---|---|
|CCGGCTTCCA|TCCGAGTACG|TGCTCGCTCG|ATGCGATGTT|TCGCTTGGTG|GTCGAATGGG|3120|
|CAGGTAGCCG|GATCAAGCGT|ATGCAGCCGC|CGCATTGCAT|CAGCCATGAT|GGATACTTTC|3180|
|TCGGCAGGAG|CAAGGTGAGA|TGACAGGAGA|TCCTGCCCCG|GCACTTCGCC|CAATAGCAGC|3240|
|CAGTCCCTTC|CCGCTTCAGT|GACAACGTCG|AGCACAGCTG|CGCAAGGAAC|GCCCGTCGTG|3300|
|GCCAGCCACG|ATAGCCGCGC|TGCCTCGTCC|TGCAGTTCAT|TCAGGGCACC|GGACAGGTCG|3360|
|GTCTTGACAA|AAAGAACCGG|GCGCCCCTGC|GCTGACAGCC|GGAACACGGC|GGCATCAGAG|3420|
|CAGCCGATTG|TCTGTTGTGC|CCAGTCATAG|CCGAATAGCC|TCTCCACCCA|AGCGGCCGGA|3480|
|GAACCTGCGT|GCAATCCATC|TTGTTCAATC|ATGCGAAACG|ATCCTCATCC|TGTCTCTTGA|3540|
|TCAGATCTTG|ATCCCCTGCG|CCATCAGATC|CTTGGCGGCA|AGAAAGCCAT|CCAGTTTACT|3600|
|TTGCAGGGCT|TCCCAACCTT|ACCAGAGGGC|GCCCCAGCTG|GCAATTCCGG|TTCGCTTGCT|3660|
|GTCCATAAAA|CCGCCCAGTC|TAGCTATCGC|CATGTAAGCC|CACTGCAAGC|TACCTGCTTT|3720|
|CTCTTTGCGC|TTGCGTTTTC|CCTTGTCCAG|ATAGCCCAGT|AGCTGACATT|CATCCGGGGT|3780|
|CAGCACCGTT|TCTGCGGACT|GGCTTTCTAC|GTGTTCCGCT|TCCTTTAGCA|GCCCTTGCGC|3840|
|CCTGAGTGCT|TGCGGCAGCG|TGAAGCTTAA|AAAACTGCAA|AAAATAGTTT|GACTTGTGAG|3900|
|CGGATAACAA|TTAAGATGTA|CCCAATTGTG|AGCGGATAAC|AATTTCACAC|ATTAAAGAGG|3960|
|AGAAATTACA|TATG| | | | |3974|

(2) INFORMATION FOR SEQ ID NO: 15:

(i) SEQUENCE CHARACTERISTICS:
        (A) LENGTH: 112 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 15:

| | | | | | |
|---|---|---|---|---|---|
|AAGCTTAAAA|AACTGCAAAA|AATAGTTTGA|CTTGTGAGCG|GATAACAATT|AAGATGTACC|60|
|CAATTGTGAG|CGGATAACAA|TTTCACACAT|TAAAGAGGAG|AAATTACATA|TG|112|

PANCREAS-DERIVED PLASMINOGEN ACTIVATOR INHIBITOR

This application is a divisional of U.S. application Ser. No. 09/902,684, filed Jul. 12, 2001, now U.S. Pat. No. 6,649,738, which is a divisional of U.S. application Ser. No. 09/026,408, filed Feb. 19, 1998, now U.S. Pat. No. 6,303,338, which is herein incorporated by reference; said U.S. application Ser. No. 09/026,408 is a continuation-in-part of U.S. application Ser. No. 08/934,011, filed Aug. 15, 1997, now abandoned, incorporated by reference; said U.S. application Ser. No. 08/934,011 claims benefit under 35 U.S.C. § 119(e) of U.S. Provisional Application No. 60/024,056, filed Aug. 16, 1996, which is herein incorporated by reference.

BACKGROUND OF THE INVENTION

1. Field of the Invention

The present invention relates to a novel member of the serine protease inhibitor (serpin) superfamily of proteins, in particular the plasminogen activator inhibitor (PAI) protein family. More specifically, isolated nucleic acid molecules are provided encoding the pancreas-derived plasminogen activator inhibitor (PAPAI) protein. Plasminogen activator inhibitor polypeptides are also provided. The present invention further relates to methods for treating physiologic and pathologic disease conditions and diagnostic methods for detecting pathologic disorders.

2. Related Art

The mammalian serine protease inhibitors (serpins) are a superfamily of single chain proteins that contain a conserved structure of approximately 370 amino acids and generally range between 40 and 60 kDa in molecular mass. $\alpha_1$-Antitrypsin (also known as $\alpha_1$-proteinase inhibitor) is a characteristic member of the serpin family in that it is a single chain glycoprotein of nearly 400 amino acid residues that functions by forming a tight 1:1 complex with its cognate protease, neutrophil (leucocyte) elastase, which subsequently slowly dissociates to yield active enzyme and inactive cleaved inhibitor (Carrell, R. W. et al., *Cold Spring Harbor Symposia on Quantitative Biology* 52:527–535 (1987)). The reactive center of the serpins is typically formed by an X-Ser that acts as a substrate for the target serine protease: $\alpha_1$-antitrypsin has a Met-Ser reactive center with the methionine residue providing a putative cleavage site for neutrophil elastase.

The majority of serpins function as protease inhibitors and so are involved in regulation of several proteinase-activated physiological processes, such as blood coagulation, fibrinolysis, complement activation, extracellular matrix turnover, cell migration and prohormone activation (Potempa, J. et al., *J. Biol. Chem.* 269:15957–19560 (1994)). As noted, serpins inhibit proteolytic events by forming a 1:1 stoichiometric complex with the active site of their cognate proteinases, which is resistant to denaturants (Cohen, A. B. et al., *Biochemistry* 17:392–400 (1987). The serpins include, but are not limited to, $\alpha_1$-antitrypsin ($\alpha_1$-proteinase inhibitor), antithrombin III, plasminogen activator inhibitor 1 (PAI-1), plasminogen activator inhibitor 2 (PAI-2), $\alpha_1$-antichymotrypsin, and $\alpha_2$-antiplasmin (Huber, R. and Carrell, R. W., *Biochemistry* 28:8951–8966 (1989).

The plasminogen activator system is responsible for the degradation of intravascular blood clots, and also contributes to extracellular proteolysis in a wide variety of physiological processes of normal development and pathological processes in the etiology of diseases such as tumor invasion and metastasis (Andreasen, P.-A., et al., *Int. J. Cancer* 72(1):1–22 (1997); Schmitt, M., et al., *Thromb. Haemost.* 78(1):285–296 (1997)). trypsin-like protease, is generated from its precursor plasminogen by the action of plasminogen activators, of which there are two types: tissue-type plasminogen activator (also known as tissue plasminogen activator) and urokinase. Plasmin degrades fibrin and several extracellular matrix and adhesion proteins and activates procollagenases.

Plasminogen activation is a highly regulated process. Precise, coordinated, spatial and temporal regulation is afforded by the interaction of a variety of mechanisms. These mechanisms include (1) inhibition by specific plasmin and plasminogen activator inhibitors; (2) binding of plasminogen, plasminogen activators, and inhibitors to fibrin, extracellular matrix proteins, and specific cell surface receptors; (3) release of tissue plasminogen activator and inhibitors from intracellular storage granules; (4) regulation of gene expression of plasminogen activators and inhibitors; (5) an autocrine feedback loop whereby plasmin-mediated activation of latent forms of growth factors regulates the expression of activators and inhibitors; and (6) clearance of free and inhibitor-bound activators via receptors (Bachmann, F. et al., *Fibrinolysis*, in: *Thrombosis Haemostasis* 1987, Verstraete, M. et al., eds., Leuven University Press (1987); Danø, K. et al., *Adv. Cancer Res.* 44:139 (1985); Pöllanen, J. et al., *Adv. Cancer Res.* 57:273 (1991); Vassalli, J. D. et al., *J. Clin. Invest.* 88:1067 (1991); Carmeliet, P. et al., *Thromb. Haemost.* 74:429 (1995); Andreasen, P. A. et al., *Mol. Cell. Endocrinol.* 68:1 (1990); Loskutoff, D. J., *Fibrinolysis* 5:197 (1991); Keski-Oja, J. et al., *Semin. Thromb. Hemost.* 17:231 (1991); Blasi, F., *BioEssays* 15:105 (1993); Andreasen, P. A. et al., *FEBS Lett.* 338:239 (1994); Bu, G. et al., *Blood* 83:3427 (1994); and Camani, C. et al., *Int. J. Hematol.* 60:97 (1994)).

Strong clinical and experimental evidences have strongly suggested an important and apparently causal role for the tumor-associated urokinase-type PA (u-PA) and the receptor u-PAR in cancer invasion and metastasis (Andreasen, P.-A., et al., *Int. J. Cancer* 72(1):1–22 (1997); Schmitt, M., et al., *Thromb. Haemost.* 78(1):285–296 (1997); Duggan, C., et al., *Br. J. Cancer* 76(5):622–627 (1997)). Consistent with its role in cancer metastasis, overexpression and unrestrained activity of u-PA has been shown to be a prognostic marker in many different types of human cancer (Schmitt, M., et al., *Fibrinolysis* 6(Suppl. 4):3–26 (1992); Schmitt, M., et al., *J. Obstet. Gynaecol.* 21:151–165 (1995); Brunner, N., et al., *Cancer Treat. Res.* 71:299–309 (1994); Kuhn, W., et al., *Gynecol. Oncol.* 55:401–409 (1994); Ganesh, S., et al., *Cancer Res.* 54:4065–4071 (1994); Nekarda, H., et al., *Cancer Res.* 54:2900–2907 (1994); Duffy, M.-J., *J. Clin. Cancer Res.* 2:613–618 (1996)). The down-regulation of u-PA may occur at the levels of transcriptional regulation of the genes and through interaction with specific endogenous inhibitors such as plasminogen activator inhibitor (PAI).

Only two plasminogen activator inhibitors are known. These are plasminogen activator inhibitor 1 and 2 (PAI-1 and PAI-2, respectively). PAI-1 and PAI-2 regulate mitogenesis, adhesion of myeloid cells, fusion of myoblasts, and migration of endothelial cells (Fazioli, F. et al., *Trends Pharm. Sci.* 15:25–29 (1995)). Indeed, PAI-1 and PAI-2 are involved in many physiological and pathological processes, including normal pregnancy, preeclampsia, intrauterine growth retardation, wound healing, tumor cell invasion and metastasis, inflammation and arthritis, inflammatory bowel disease, appendicitis, complications from systemic lupus erythematosus, ovulation and prostatic involution and osteonecrosis (Kruithof, E. K. O. et al., *Blood* 86:4007 (1995)).

Both PAI-1 and PAI-2 have been shown to inhibit extracellular matrix degradation in vitro (Cajot, J.-F., et al., *Proc. Natl. Acad. Sci. USA* 87:6939–6943 (1990); Baker, M.-S., et al., *Cancer Res.* 50:4676–4684 (1990)). These results suggest that the inhibitory activity of PAIs might be important in inhibiting tumor malignant progression leading to metastasis. In fact, administration of a recombinant PAI-2 to mice decreases tumor growth (Astedt, B., et al., *Fibrinol.* 9:175–177 (1995)), whereas overexpression of either PAI-1 or PAI-2 inhibits tumor metastasis (Muller, B., et al., *Proc. Natl. Acad. Sci. USA* 92:205–209 (1995); Soff, G.-A., et al., *J. Clin. Invest.* 96:2593–2600 (1995)).

In breast cancer, it has been demonstrated extensively that uPA and PAI-1 are statistically independent, strong prognostic factors for disease free and overall survival, i.e., high tumor levels are associated with a poor prognosis and are conductive to tumor cell spread and metastasis (Brunner, N., et al., *Cancer Treat. Res.* 71:299–309 (1994); Duffy, M., et al., *Cancer* 62:531–533 (1988); Duggan, C., et al., *Int. J. Cancer* 61:597–600(1995); Schmitt, M., et al., *Br. J. Cancer* 76(3):306–311 (1997)). Immunohistochemical staining has detected PAI-I expression at stromal fibroblasts surrounding tumor nodules or at tumor margins (Bianchi, E., et al., *Int. J. Cancer* 60:597–603 (1995)). The production of PAI-I by the tumor stroma may represent a host defensive response to the excessive proteolysis. In contrast to PAI-I, high level PAI-2 expression may be a favorable prognostic marker in breast cancer (Schmitt, M., et al., *Thromb. Haemost.* 78(1):285–296 (1997); Duggan, C., et al., *Br. J. Cancer* 76(5):622–627 (1997)). In breast carcinomas with high uPA values, PAI-2 was associated with a prolonged relapse-free survival, metastasis-free survival, and overall survival (Bouchet, C., et al., *Br. J. Cancer* 69:398–405 (1994)). In relation to the clinicopathological findings, an inverse correlation between PAI-2 mRNA expression and lymph node metastasis was demonstrated in breast cancers (Sumiyoshi, K., et al., *S.Int. J. Cancer* 50:345–348 (1992)). In this study, the expression of uPA and PAI-1 was significantly correlated with negative expression of PAI-2; and a low level of PAI-2 expression was significantly associated with lymph node involvement (Sumiyoshi, K., et al., *Int. J. Cancer* 50:345–348 (1992)). PAI-2 expression is detected predominantly in malignant mammary epithelial cells of primary carcinomas but is also present in stromal cells (Andreasen, P.-A., et al., *Int. J. Cancer* 72(1): 1–22 (1997)). These results indicate that PAI-2 may play a critical role in inhibition of extracellular matrix degradation mediated by plasminogen activator during tumor cell invasion and metastasis.

In view of the wide range of roles that plasminogen activator inhibitors play in physiologic and pathologic processes, there is a continuing need for the isolation and characterization of novel plasminogen activator inhibitors.

SUMMARY OF THE INVENTION

The present invention provides isolated nucleic acid molecules comprising a polynucleotide encoding the pancreas-derived plasminogen activator inhibitor (PAPAI) polypeptide having the amino acid sequence is shown in FIGS. 1A–1B (SEQ ID NO:2), FIGS. 4A–4B (SEQ ID NO:13) or the amino acid sequence encoded by the cDNA clone deposited in a bacterial host as ATCC Deposit Number 97657 on Jul. 12, 1996. The nucleotide sequence determined by sequencing the deposited PAPAI clone, which is shown in FIGS. 4A–4B, contains an open reading frame encoding a polypeptide of 405 amino acid residues, including an initiation codon at positions 67–69, with a leader sequence of about 18 amino acid residues, and a deduced molecular weight of about 46 kDa. The amino acid sequence of the mature PAPAI protein is shown in SEQ ID NO:13 (amino acid residues from about 1 to about 387 in SEQ ID NO:13). Another sequence of a PAPAI clone which is shown in FIGS. 1A–1B (SEQ ID NO:1), contains an open reading frame encoding a polypeptide of 392 amino acid residues, including an initiation codon at positions 67–69, with a leader sequence of about 14 amino acid residues, and a deduced molecular weight of about 44.5 kDa. The amino acid sequence of this mature PAPAI protein is shown in SEQ ID NO:2 (amino acid residues from about 1 to about 378 in SEQ ID NO:2).

Thus, one aspect of the invention provides an isolated nucleic acid molecule comprising a polynucleotide having a nucleotide sequence selected from the group consisting of: (a) a nucleotide sequence encoding the PAPAI polypeptide having the complete amino acid sequence in SEQ ID NO:2; (b) a nucleotide sequence encoding the PAPAI polypeptide having the complete amino acid sequence in SEQ ID NO:2 but minus the N-terminal methionine residue; (c) a nucleotide sequence encoding the mature PAPAI polypeptide having the amino acid sequence at positions 1–378 in SEQ ID NO:2; (d) a nucleotide sequence encoding the PAPAI polypeptide having the complete amino acid sequence in SEQ ID NO:13; (e) a nucleotide sequence encoding the PAPAI polypeptide having the complete amino acid sequence in SEQ ID NO:13, but minus the N-terminal methionine residue; (f) a nucleotide sequence encoding the mature PAPAI polypeptide having the amino acid sequence at positions 1–387 in SEQ ID NO:13; (g) a nucleotide sequence encoding the PAPAI polypeptide having the complete amino acid sequence encoded by the cDNA clone contained in ATCC Deposit No. 97657; (h) a nucleotide sequence encoding the mature PAPAI polypeptide having the amino acid sequence encoded by the cDNA clone contained in ATCC Deposit No. 97657; and (i) a nucleotide sequence complementary to any of the nucleotide sequences in (a), (b), (c), (d), (e), (f), (g), or (h) above.

Further embodiments of the invention include isolated nucleic acid molecules that comprise a polynucleotide having a nucleotide sequence at least 95% identical, and more preferably at least 96%, 97%, 98% or 99% identical, to any of the nucleotide sequences in (a), (b), (c), (d), (e), (f), (g), (h), or (i) above, or a polynucleotide which hybridizes under stringent hybridization conditions to a polynucleotide in (a), (b), (c), (d), (e), (f), (g), (h), or (i) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a PAPAI polypeptide having an amino acid sequence in (a), (b), (c), (d), (e), (f), (g), (h), or (i) above.

The present invention also relates to recombinant vectors, which include the isolated nucleic acid molecules of the present invention, and to host cells containing the recombinant vectors, as well as to methods of making such vectors and host cells and for using them for production of PAPAI polypeptides or peptides by recombinant techniques.

The invention further provides an isolated PAPAI polypeptide having amino acid sequence selected from the group consisting of: (a) the amino acid sequence of the PAPAI polypeptide having the complete 392 amino acid sequence, including the leader sequence shown in SEQ ID NO:2; (b) the amino acid sequence of the PAPAI polypeptide having the complete 392 amino acid sequence, including the leader sequence shown in SEQ ID NO:2, but minus the N-terminal methionine residue; (c) the amino acid sequence of the mature PAPAI polypeptide (without the leader) having the amino acid sequence at positions 1–378 in SEQ ID NO:2; (d) the amino acid sequence of the PAPAI polypeptide having the complete 405 amino acid sequence, including the leader sequence shown in SEQ ID NO:13; (e) the amino acid sequence of the PAPAI polypeptide having the complete 405 amino acid sequence, including the leader sequence shown in SEQ ID NO:13, but minus the N-terminal methionine residue; (f) the amino acid sequence of the mature PAPAI polypeptide (without the leaser) having the amino acid sequence at positions 1–387 in SEQ ID NO:13; (g) the amino acid sequence of the PAPAI polypeptide having the complete amino acid sequence, including the leader, encoded by the cDNA clone contained in ATCC Deposit No. 97657; and (h) the amino acid sequence of the mature PAPAI polypeptide having the amino acid sequence encoded by the cDNA clone contained in ATCC Deposit No. 97657. The polypeptides of the present invention also include polypeptides having an amino acid sequence at least 95% identical, more preferably at least 96%, 97%, 98% or 99% identical to those above.

An additional embodiment of this aspect of the invention relates to a peptide or polypeptide which has the amino acid sequence of an epitope-bearing portion of a PAPAI polypeptide having an amino acid sequence described in (a), (b), (c), (d), (e), (f), (g), or (h) above. Peptides or polypeptides having the amino acid sequence of an epitope-bearing portion of a PAPAI polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a PAPAI polypeptide having an amino acid sequence described in (a), (b), (c), (d), (e), (f), (g), or (h) above.

For a number of pathologic disorders, such as tumor invasion and metastasis, significant alterations (increases or decreases) in level of PAPAI gene expression can be detected in a sample of tissue or bodily fluid. Increased or decreased levels of PAPAI gene expression can be measured, in such a sample, relative to a "standard" PAPAI gene expression level, i.e., the PAPAI expression level in a tissue or bodily fluid from an individual not having the disorder. Thus, the present invention provides a diagnostic method useful during diagnosis of such disorders, which involves assaying the expression level of the gene encoding the PAPAI protein in tissue or bodily fluid from an individual and comparing the gene expression level with a standard PAPAI gene expression level, whereby an increase or decrease in the gene expression level over the standard is indicative of a pathologic disorder, such as tumor invasion and metastasis, hemorrhage in liver disease, and preeclampsia.

The PAPAI protein inhibits the plasminogen activator system when administered to an individual. The plasminogen activator system is responsible for the degradation of intravascular blood clots, while also contributing to extracellular proteolysis in a wide variety of physiological processes (e.g. wound healing, cell migration, tissue remodeling, angiogenesis, trophoblast implantation, ovulation and fetal development) and pathological processes (e.g. tumor invasion and metastasis, intrauterine growth retardation, preeclampsia, and acute and chronic inflammation). Thus, by the invention, methods are provided for inhibiting the plasminogen activator system, which involve administering an inhibitory amount of PAPAI either alone or together with one or more plasminogen activator inhibitors, such as PAI-I and PAI-2.

BRIEF DESCRIPTION OF THE FIGURES

FIGS. 1A–1B show the nucleotide (SEQ ID NO:1) and deduced amino acid (SEQ ID NO:2) sequences of pancreas-derived plasminogen activator inhibitor (PAPAI) protein. The protein has a leader sequence of about 14 amino acid residues (underlined) and a deduced molecular weight of about 44.5 kDa. The predicted amino acid sequence of the mature PAPAI protein is also shown in FIGS. 1A–1B (SEQ ID NO:2).

FIGS. 2A–2C show the regions of similarity between the amino acid sequences of the PAPAI protein (HPASD50P protein) and human plasminogen activator inhibitor 1 (PAI-1) (SEQ ID NO:3) and human plasminogen activator inhibitor 2 (PAI-2) (SEQ ID NO:4).

FIGS. 4A–4B show the nucleotide (SEQ ID NO:12) and deduced amino acid (SEQ ID NO:13) sequences of PAPAI, which was determined by sequencing the cDNA clone deposited as ATCC Deposit No. 97657. The protein has a leader sequence of about 18 amino acid residues (underlined) and a deduced molecular weight of about 46 kDa.

FIG. 6 shows the nucleotide sequence of the regulatory elements of the pHE promoter (SEQ ID NO:15). The two lac operator sequences, the Shine-Delgarno sequence (S/D), and the terminal HindIII and NdeI restriction sites (italicized) are indicated.

DETAILED DESCRIPTION

Figure 3:
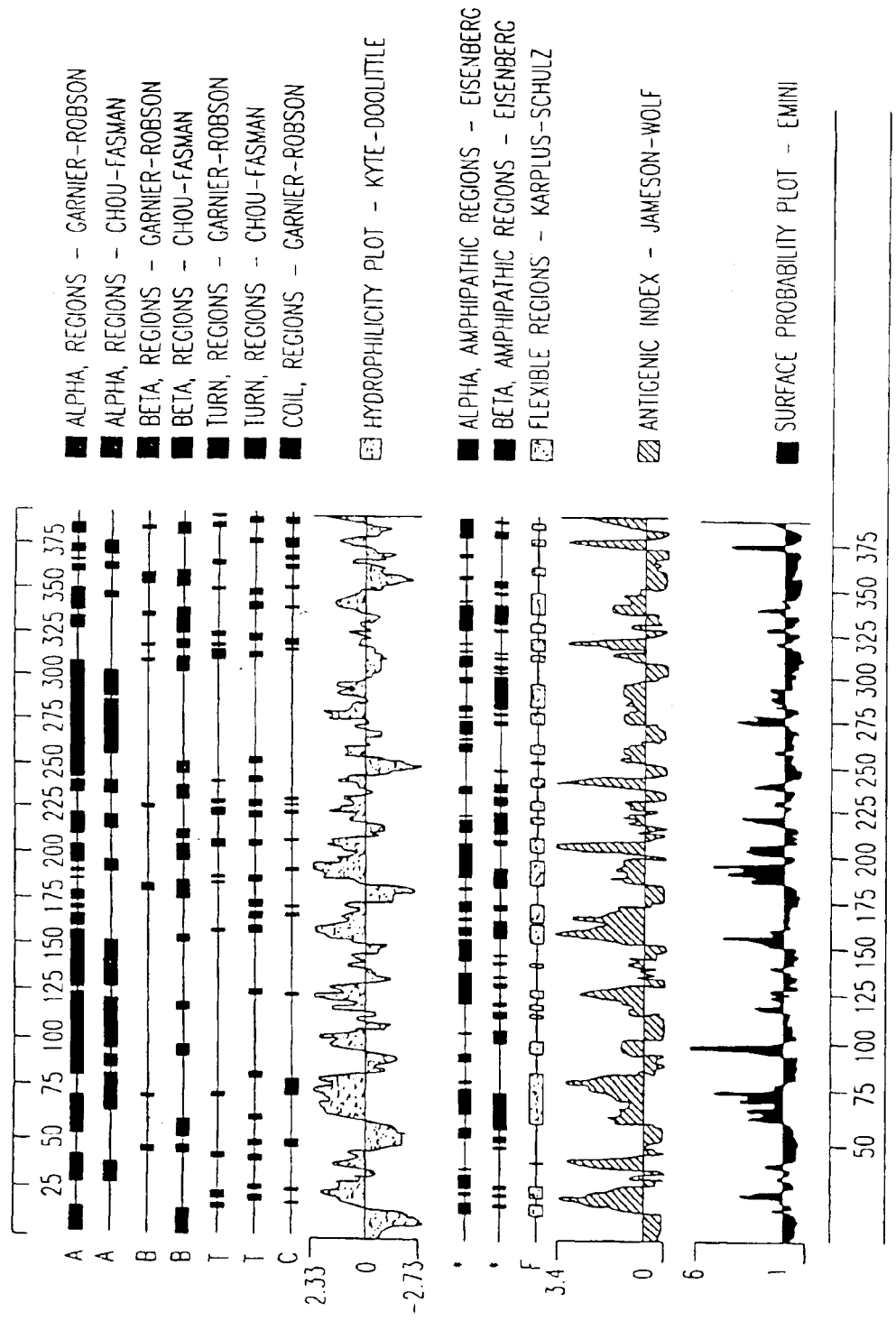
FIG. 3 shows an analysis of the predicted alpha, beta, turn, and coil regions, and the predicted hydrophilicity, amphipathic nature, flexible regions, antigenic index, and surface probability plot of the of the polypeptide of FIGS. 1A–1B (SEQ ID NO: 2) and FIGS. 4A–4B (SEQ ID NO:13). In the "Antigenic Index—Jameson-Wolf" graph, amino acid residues about 20 to about 30, about 45 to about 50, about 60 to about 90, about 125 to about 135, about 160 to about 175, about 220 to about 225, about 250 to about 260, about 320 to about 330, and about 375 to about 380 in FIGS. 1A–1B and FIGS. 4A–4B correspond to the highly antigenic regions of the PAPAI protein. These highly antigenic fragments in FIGS. 1A–1B correspond to the following fragments, respectively, in SEQ ID NO:2: amino acid residues about 6 to about 16, about 31 to about 36, about 46 to about 76, about 111 to about 121, about 146 to about 161, about 206 to about 211, about 236 to about 246, about 306 to about 316, and about 361 to about 366. These highly antigenic fragments in FIGS. 4A–4B correspond to the following fragments, respectively, in SEQ ID NO:13: amino acid residues about 2 to about 12, about 27 to about 32, about 42 to about 72, about 107 to about 117, about 142 to about 157, about 202 to about 207, about 232 to about 242, about 302 to about 312, and about 357 to about 362.

The present invention provides isolated nucleic acid molecules comprising a polynucleotide encoding a PAPAI polypeptide, having the amino acid sequence shown in FIGS. 4A–4B (SEQ ID NO:13), which was determined by sequencing a cloned cDNA, or in FIGS. 1A–1B (SEQ ID NO:2). The PAPAI protein of the present invention shares sequence homology with human plasminogen activator inhibitor 1 (PAI-1) (SEQ ID NO:3) and human plasminogen activator 2 (PAI-2)(SEQ ID NO:4). The nucleotide sequence shown in FIGS. 4A–4B (SEQ ID NO:13) was obtained by sequencing the HPASD50P clone, which was deposited on Jul. 12, 1996 at the American Type Culture Collection, Patent Depository, 10801 University Boulevard, Manassas, Va., 20110-2209, and given accession number 97657.

Accordingly, in one embodiment of the present invention, isolated nucleic acid molecules are provided which encode the PAPAI protein. PAPAI is a novel member of the plasminogen activator inhibitor subfamily.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Figure 2A:
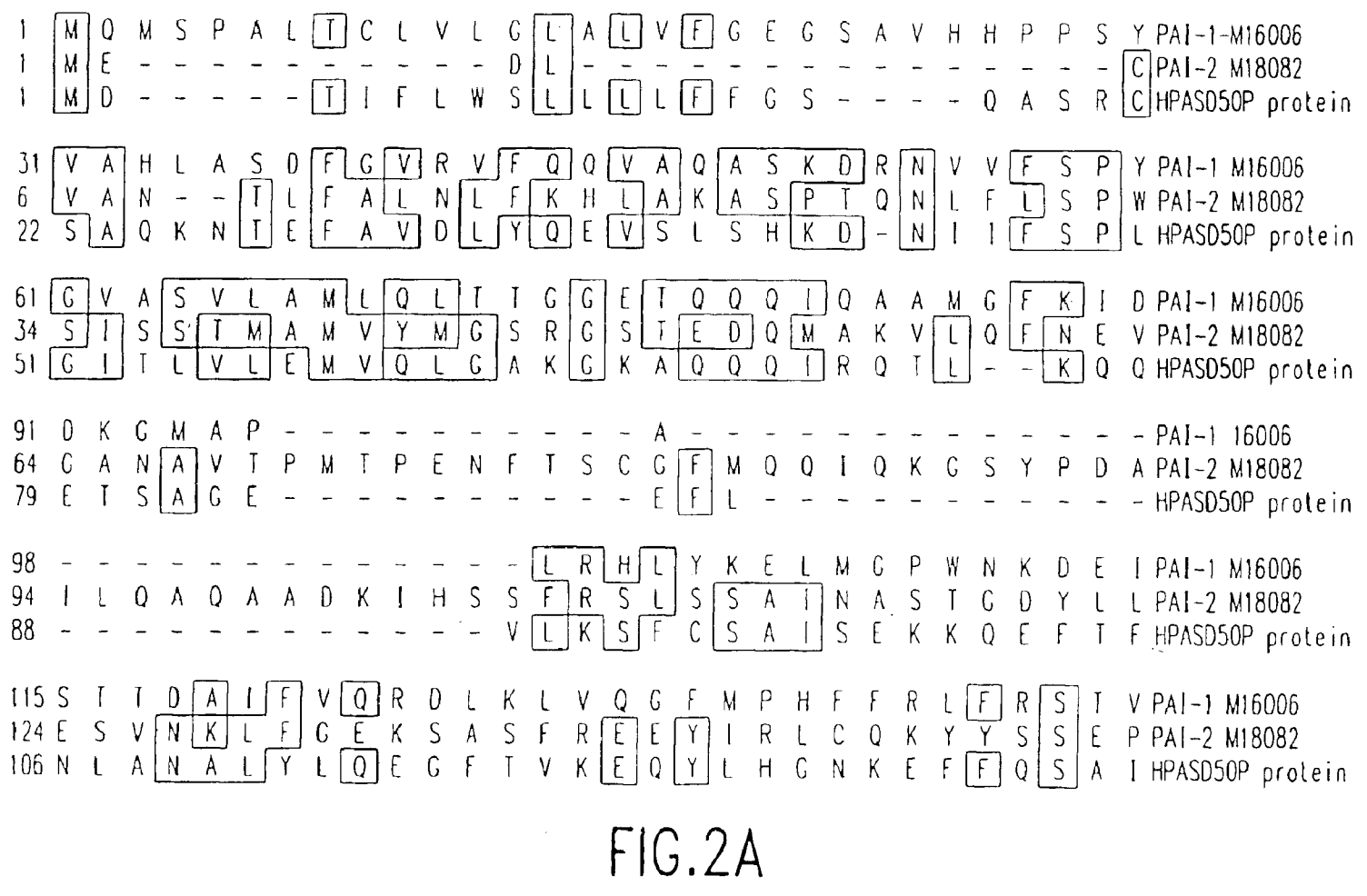
Figure 2B:
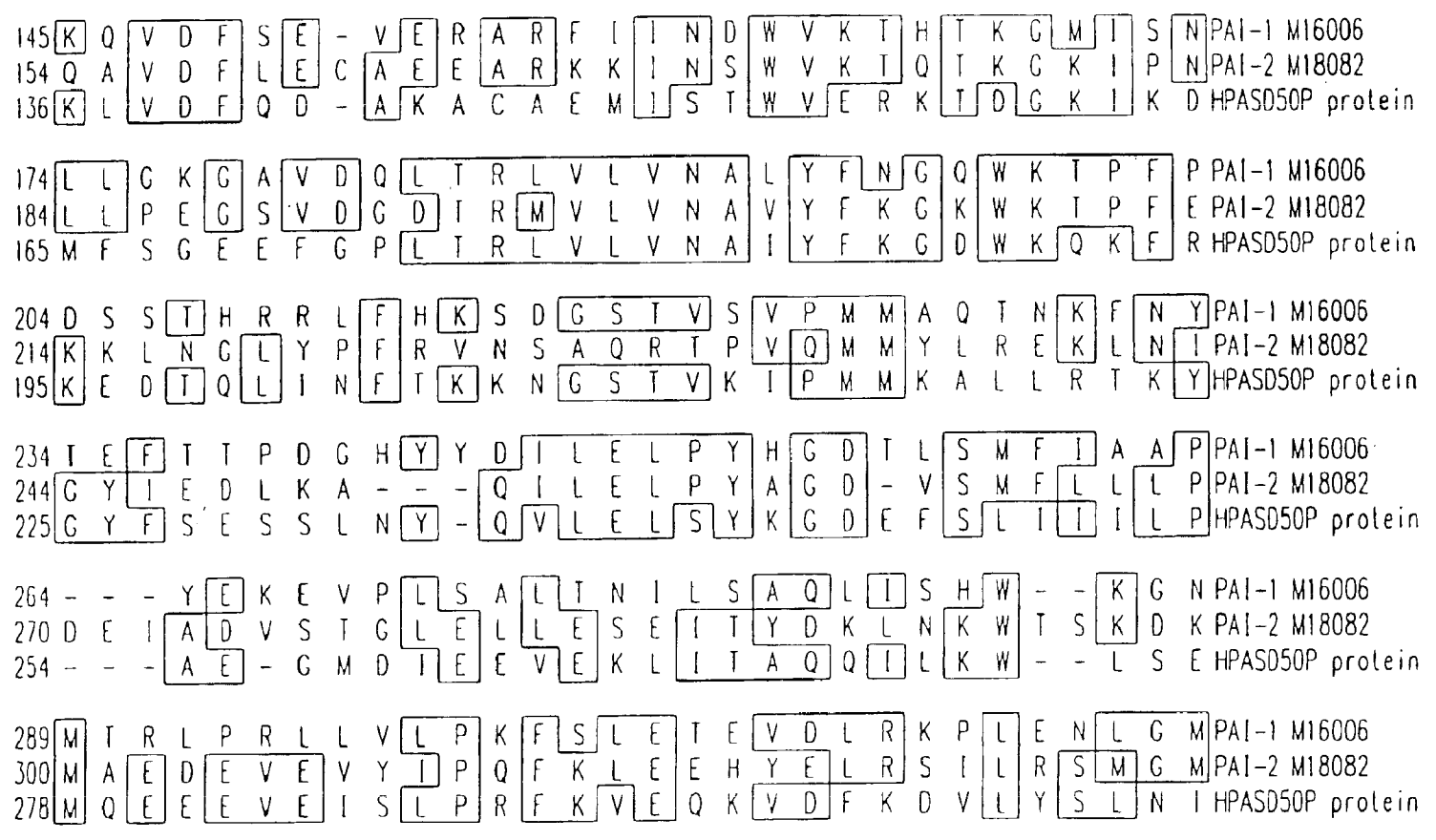

Using the information provided herein, such as the nucleotide sequence in SEQ ID NO:1 or SEQ ID NO:12, a nucleic acid molecule of the present invention encoding a PAPAI polypeptide may be obtained using standard cloning and screening procedures, such as those for cloning cDNAs using mRNA as starting material. Illustrative of the invention, the nucleic acid molecules described in SEQ ID NO:1 and SEQ ID NO:12 were discovered in a cDNA library derived from human pancreatic tissue. The determined nucleotide sequence of the PAPAI cDNA of SEQ ID NO:1 contains an open reading frame encoding a protein of 392 amino acid residues, with an initiation codon at positions 67–69 of the nucleotide sequence in SEQ ID NO:1, a predicted leader sequence of about 14 amino acid residues, and a deduced molecular weight of about 44.5 kDa. The amino acid sequence of the predicted mature PAPAI is shown in SEQ ID NO:2 from amino acid residue 1 to residue 378. The PAPAI protein shown in SEQ ID NO:2 is about 67% and 68% identical to PAI-1 (SEQ ID NO:3) and PAI-2 (SEQ ID NO:4), respectively (FIGS. 2A–2C). The determined nucleotide sequence of the PAPAI cDNA of SEQ ID NO:12 contains an open reading frame encoding a protein of 405 amino acid residues, with an initiation codon at positions 67–69 of the nucleotide sequence in SEQ ID NO:12, a predicted leader sequence of about 18 amino acid residues, and a deduced molecular weight of about 46 kDa. The amino acid sequence of the predicted mature PAPAI is shown in SEQ ID NO:13 from amino acid residue 1 to residue 387. The PAPAI protein shown in SEQ ID NO:12 was determined by sequencing the deposited clone. As one of ordinary skill would appreciate, due to the possibilities of sequencing errors discussed above, as well as the variability of cleavage sites for leaders in different known proteins, the actual PAPAI polypeptide encoded by the deposited cDNA comprises about 405 amino acids, but may be anywhere in the range of 385–425 amino acids; and the actual leader sequence of this protein is about 18 amino acids, but may be anywhere in the range of about 10 to about 26 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 67–69 of the nucleotide sequence shown in SEQ ID NO:1; DNA molecules comprising the coding sequence for the mature PAPAI protein shown in FIGS. 1A–1B (last 378 amino acids) (SEQ ID NO:2); DNA molecules comprising an ORF with an initiation codon at positions 67–69 of the nucleotide sequence shown in SEQ ID NO:12; DNA molecules comprising the coding sequence for the mature PAPAI protein shown in FIGS. 4A–4B (last 387 amino acids); and DNA molecules which comprise a sequence substantially different from those described above but which, due to the degeneracy of the genetic code, still encode the PAPAI protein. Of course, the genetic code is well known in the art. Thus, it would be routine for one skilled in the art to generate the degenerate variants described above.

In addition, the present inventors have identified nucleic acid molecules having nucleotide sequences related to extensive portions of SEQ ID NO:1 which have been determined from the following related cDNA clones: HPASD50R (SEQ ID NO:10) and HBXFM84RA (SEQ ID NO:11).

In another aspect, the invention provides isolated nucleic acid molecules encoding the PAPAI polypeptide having an amino acid sequence encoded by the cDNA clone contained in the plasmid deposited as ATCC Deposit No. 97657 on Jul. 12, 1996. In a further embodiment, nucleic acid molecules are provided encoding the mature PAPAI polypeptide or full-length PAPAI polypeptide lacking the N-terminal methionine residue. The invention further provides an isolated nucleic acid molecule having the nucleotide sequence shown in SEQ ID NO:1 or the nucleotide sequence of the PAPAI cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the PAPAI gene in human tissue, for instance, by Northern blot analysis.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97657. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 $\mu$g/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50, 100, 150, 200, 250, 300, 350, 400, 450, 500, 650, 700, 750, 800, 850, 900, 950, 1000, 1050, or 1100 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in SEQ ID NO:1 or SEQ ID NO:12. By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1 or SEQ ID NO:12). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, edited by Sambrook, J., Fritsch, E. F. and Maniatis, T., (1989), Cold Spring Harbor Laboratory Press, the entire disclosure of which is hereby incorporated herein by reference.

Since a PAPAI cDNA clone has been deposited and its determined nucleotide sequence is provided in SEQ ID NO:1 and SEQ ID NO:12, generating polynucleotides which hybridize to a portion of the PAPAI cDNA molecule would be routine to the skilled artisan. For example, restriction endonuclease cleavage or shearing by sonication of the PAPAI cDNA clone could easily be used to generate DNA portions of various sizes which are polynucleotides that hybridize to a portion of the PAPAI cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the PAPAI cDNA shown in FIGS. 1A–1B (SEQ ID NO:1) or FIGS. 4A–4B (SEQ ID NO:12)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The invention further provides isolated nucleic acid molecules comprising a polynucleotide encoding an epitope-bearing portion of the PAPAI protein. In particular, isolated nucleic acid molecules of the present invention include nucleic acid molecules encoding: a polypeptide comprising amino acid residues from about 6 to about 16 in SEQ ID NO:2; a polypeptide comprising amino acid residues from about 31 to about 36 in SEQ ID NO:2; a polypeptide comprising amino acid residues from about 46 to about 76 in SEQ ID NO:2; a polypeptide comprising amino acid residues from about 111 to about 121 in SEQ ID NO:2; a polypeptide comprising amino acid residues from about 146 to about 161 in SEQ ID NO:2; a polypeptide comprising amino acid residues from about 206 to about 211 in SEQ ID NO:2; a polypeptide comprising amino acid residues from about 236 to about 246 in SEQ ID NO:2; a polypeptide comprising amino acid residues from about 306 to about 316 in SEQ ID NO:2; a polypeptide comprising amino acid residues from about 361 to about 366 in SEQ ID NO:2; a polypeptide comprising amino acid residues from about 2 to about 12 in SEQ ID NO:13; a polypeptide comprising amino acid residues from about 27 to about 32 in SEQ ID NO:13; a polypeptide comprising amino acid residues from about 42 to about 72 in SEQ ID NO:13; a polypeptide comprising amino acid residues from about 107 to about 117 in SEQ ID NO:13; a polypeptide comprising amino acid residues from about 142 to about 157 in SEQ ID NO:13; a polypeptide comprising amino acid residues from about 202 to about 207 in SEQ ID NO:13; a polypeptide comprising amino acid residues from about 232 to about 242 in SEQ ID NO:13; a polypeptide comprising amino acid residues from about 302 to about 312 in SEQ ID NO:13; and a polypeptide comprising amino acid residues from about 357 to about 362 in SEQ ID NO:13. Methods for generating such epitope-bearing portions of PAPAI are described in detail below.

As indicated, nucleic acid molecules of the present invention which encode a PAPAI polypeptide may include, but are not limited to those encoding the amino acid sequence of the mature polypeptide, by itself; the coding sequence for the mature polypeptide and additional sequences, such as those encoding the about 14 amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984).

The present invention further relates to variants of the nucleic acid molecules of the present invention, which encode portions, analogs or derivatives of the PAPAI protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the PAPAI protein or portions thereof. Also especially preferred in this regard are conservative substitutions. Most highly preferred are nucleic acid molecules encoding the mature PAPAI protein having the amino acid sequence shown in FIGS. 1A–1B (SEQ ID NO:2) or FIGS. 4A–4B (SEQ ID NO:13) or the mature PAPAI amino acid sequence encoded by the deposited cDNA clone.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine residue; (c) a nucleotide sequence encoding the polypeptide having the amino acid sequence at positions from about 1 to about 378 in SEQ ID NO:2; (d) a nucleotide sequence encoding the polypeptide having the amino acid sequence in SEQ ID NO:13; (e) a nucleotide sequence encoding the polypeptide having the amino acid sequence in SEQ ID NO:13, but lacking the N-terminal methionine residue; (f) a nucleotide sequence encoding the polypeptide having the amino acid sequence at positions from about 1 to about 387 in SEQ ID NO:13; (g) a nucleotide sequence encoding the polypeptide having the amino acid sequence encoded by the cDNA clone contained in ATCC Deposit No. 97657; (h) a nucleotide sequence encoded by the cDNA clone contained in ATCC Deposit No. 97657; or (i) a nucleotide sequence complementary to any of the nucleotide sequences in (a), (b), (c), (d), (e), (f), (g), or (h).

By a polynucleotide having a nucleotide sequence at least, for example, 95% "identical" to a reference nucleotide sequence encoding a PAPAI polypeptide is intended that the nucleotide sequence of the polynucleotide is identical to the reference sequence except that the polynucleotide sequence may include up to five point mutations per each 100 nucleotides of the reference nucleotide sequence encoding the PAPAI polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 or SEQ ID NO:12 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO:1 or SEQ ID NO:12 or to the nucleic acid sequence of the deposited cDNA, irrespective of whether they encode a polypeptide having PAPAI activity. This is because even where a particular nucleic acid molecule does not encode a polypeptide having PAPAI activity, one of skill in the art would still know how to use the nucleic acid molecule, for instance, as a hybridization probe or a polymerase chain reaction (PCR) primer. Uses of the nucleic acid molecules of the present invention that do not encode a polypeptide having PAPAI activity include, inter alia, (1) isolating the PAPAI gene or allelic variants thereof in a cDNA library; (2) in situ hybridization (e.g., "FISH") to metaphase chromosomal spreads to provide precise chromosomal location of the PAPAI gene, as described in Verma et al., *Human Chromosomes: A Manual of Basic Techniques*, Pergamon Press, New York (1988); and Northern Blot analysis for detecting PAPAI mRNA expression in specific tissues.

Preferred, however, are nucleic acid molecules having sequences at least 95%, 96%, 97%, 98% or 99% identical to the nucleic acid sequence shown in SEQ ID NO:1 or SEQ ID NO:12 or to the nucleic acid sequence of the deposited cDNA which do, in fact, encode a polypeptide having PAPAI protein activity. By "a polypeptide having PAPAI activity" is intended polypeptides exhibiting activity similar, but not necessarily identical, to an activity of the PAPAI protein of the invention (either the full-length protein or, preferably, the mature protein), as measured in a particular biological assay.

Assays of plasminogen activator activity are well-known to those in the art. These assays can be used to measure plasminogen activator activity of partially purified or purified native or recombinant protein. For example, an $^{125}$I fibrin lysis assay can be used (Lyon, P. B. et al., *The Prostate* 27:179–186 (1995); Unkeless, J. C. et al., *J. Exp. Med* 137:85–126 (1973)).

In this assay, $^{125}$I fibrinogen is placed into 96-well, flat bottom culture plates at a concentration of 10 µg/cm$^2$ in a volume of 10–30 µl. Dried plates are exposed to 100 µl volume of RPMI medium containing 10% fetal bovine serum. Excess thrombin in the serum results in fibrinogen conversion to fibrin with a total trypsinizable radioactivity of approximately 60,000 counts per minute per well. Into each test well is placed 1–5 IU of tissue plasminogen activator (Sigma, St. Louis, Mo.). Alternatively, if cells are used in place of tissue plasminogen activator, 1×10$^5$ cells, washed twice with phosphate-buffered saline, are placed into each test well.

Into each test well is placed 1 µg of human plasminogen and 1 to 10 µg of the partially purified or purified native or recombinant test protein, in 5–50 µl of phosphate buffered saline.

Control wells receive an equal volume (5–50 µl) of phosphate buffered saline. Each sample is assayed in duplicate or triplicate, with background values of radioactive release determined from the duplicate sample wells without plasminogen. Additional control wells include media alone, media plus plasminogen, media plus plasminogen and plasminogen activator, and wells containing up to 200 µl of 0.25% bovine trypsin to determine the maximal releasable radioactivity.

At intervals following plating, the medium is removed and radioactivity is measured by gamma counting. Plasminogen-dependent fibrinolysis is defined as the difference in supernatant radioactivity between plasminogen-containing and plasminogen-free wells. Plasminogen activator-dependent fibrinolysis is expressed as a percentage of the maximal releasable radioactivity per well. Maximal releasable radioactivity is determined by averaging the total trypsinizable radioactivity in three fibrin-coated wells. It will be apparent to one of ordinary skill in the art that the amounts of reactants and reactant conditions may have to be modified in order to practice the assay.

PAPAI inhibits plasminogen activators such as urokinase and tissue plasminogen activator. Thus, "a polypeptide having PAPAI protein activity" includes polypeptides that exhibit the plasminogen activator inhibiting activity, in the above-described assay and in a dose-dependent manner. Although the degree of dose-dependent activity need not be identical to that of the PAPAI protein, preferably, "a polypeptide having PAPAI protein activity" will exhibit substantially similar dose-dependence in a given activity as compared to the PAPAI protein (i.e., the candidate polypeptide will exhibit greater activity or not more than about tenfold less and, preferably, not more than about twofold less activity relative to the reference PAPAI protein).

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNA or the nucleic acid sequence shown in SEQ ID NO:1 or SEQ ID NO:12 will encode a polypeptide "having PAPAI protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having PAPAI protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., *supra*, and the references cited therein.

Vectors and Host Cells

The present invention also relates to vectors which include the isolated DNA molecules of the present invention, host cells which are genetically engineered with the recombinant vectors, and the production of PAPAI polypeptides or fragments thereof by recombinant techniques.

Recombinant constructs may be introduced into host cells using well known techniques such infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In addition to the use of expression vectors in the practice of the present invention, the present invention further includes novel expression vectors comprising operator and promoter elements operatively linked to nucleotide sequences encoding a protein of interest. One example of such a vector is pHE4-5 which is described in detail below.

Figure 5:
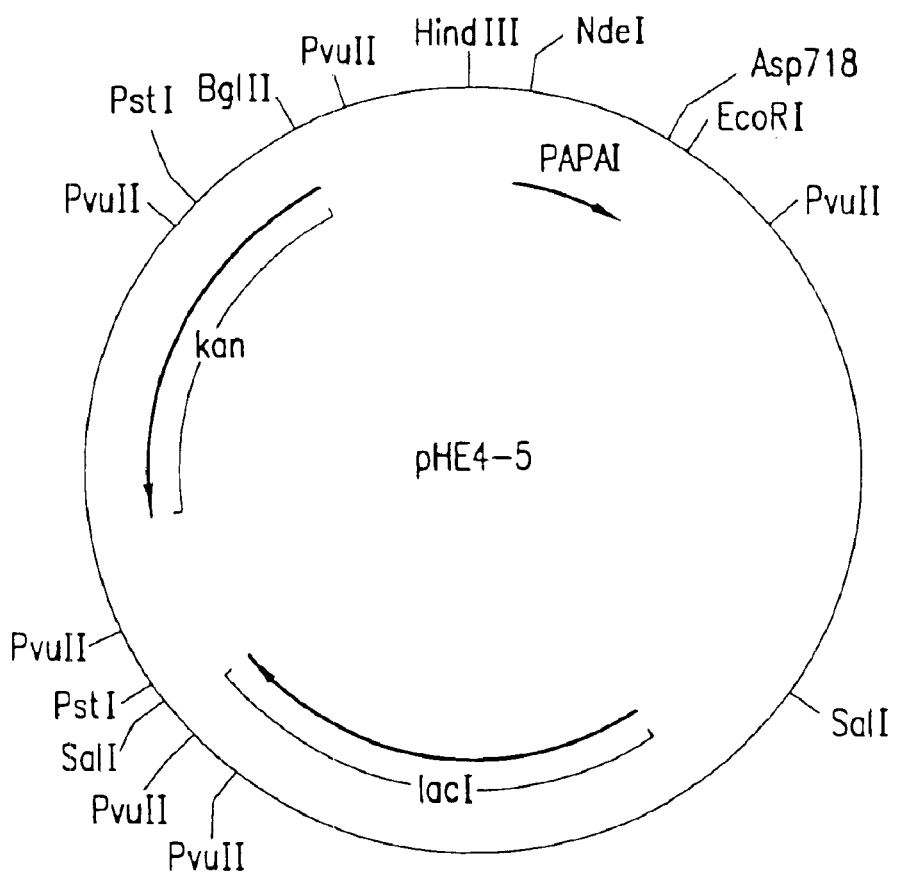
FIG. 5 shows a schematic representation of the pHE4-5 expression vector (SEQ ID NO:14) and the subcloned PAPAI cDNA coding sequence. The locations of the kanamycin resistance marker gene, the PAPAI coding sequence, the oriC sequence, and the lacIq coding sequence are indicated.

As summarized in FIGS. 5 and 6, components of the pHE4-5 vector (SEQ ID NO:14) include: 1) a neomycin-phosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. A nucleotide sequence encoding PAPAI (SEQ ID NO:2 or 13), is operatively linked to the promoter and operator by inserting the nucleotide sequence between the NdeI and Asp718 sites of the pHE4-5 vector.

As noted above, the pHE4-5 vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). PAPAI thus is not produced in appreciable quantities in uninduced host cells containing the pHE4-5 vector. Induction of these host cells by the addition of an agent such as IPTG, however, results in the expression of the PAPAI coding sequence.

The promoter/operator sequences of the pHE4-5 vector (SEQ ID NO:15) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4-5 vector except for the PAPAI coding sequence. Features of the pHE4 vectors include optimized synthetic T5 phage promoter, lac operator, and Shine-Delgamo sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgamo sequence 5' to the AUG initiation codon. Shine-Delgamo sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE-4-5 vector (SEQ ID NO:14).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification.

The PAPAI protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

PAPAI Polypeptides and Fragments

The invention further provides an isolated PAPAI polypeptide having the amino acid sequence encoded by the deposited cDNA, or the amino acid sequence in SEQ ID NO:2 or SEQ ID NO:13, or a peptide or polypeptide comprising a portion of the above polypeptides. The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the PAPAI polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the PAPAI polypeptide which show substantial PAPAI polypeptide activity or which include regions of PAPAI protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2 or SEQ ID NO:13, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the PAPAI protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

As indicated, changes are preferably of aminor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given PAPAI polypeptide will not be more than 50, 40, 30, 20, 10, 5, or 3.

Amino acids in the PAPAI protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as plasminogen activator inhibition. Sites that are critical for plasminogen activator inhibition can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the PAPAI polypeptide can be substantially purified by the one-step method described in Smith and Johnson, *Gene* 67:31–40 (1988).

The polypeptides of the present invention are preferably provided in an isolated form, and preferably are substantially purified. A recombinantly produced version of the PAPAI polypeptide can be substantially purified by the one-step method described in Smith and Johnson, *Gene* 67:31–40 (1988).

The polypeptides of the present invention include the polypeptide encoded by the deposited cDNA including the leader; the mature polypeptide encoded by the deposited the cDNA minus the leader (i.e., the mature protein); a polypeptide comprising amino acids about −14 to about 378 in SEQ ID NO:2; a polypeptide comprising amino acids about −13 to about 378 in SEQ ID NO:2; a polypeptide comprising amino acids about 1 to about 378 in SEQ ID NO:2; a polypeptide comprising amino acids about −18 to about 387 in SEQ ID NO:13; a polypeptide comprising amino acids about −17 to about 387 in SEQ ID NO:13; a polypeptide comprising amino acids about 1 to about 387 in SEQ ID NO:13; as well as polypeptides at least 95% identical, more preferably at least 96%, 97%, 98% or 99% identical to the polypeptide encoded by the deposited cDNA, to the polypeptide of SEQ ID NO:2 or SEQ ID NO:13, and also include portions of such polypeptides with at least 30 amino acids and more preferably at least 50 amino acids.

By a polypeptide having an amino acid sequence at least, for example, 95% "identical" to a reference amino acid sequence of a PAPAI polypeptide is intended that the amino acid sequence of the polypeptide is identical to the reference sequence except that the polypeptide sequence may include up to five amino acid alterations per each 100 amino acids of the reference amino acid of the PAPAI polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96% 97%, 98% or 99% identical to, for instance, the amino acid sequence shown in SEQ ID NO:2 or SEQ ID NO:13 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As described in detail below, the polypeptides of the present invention can be used to raise polyclonal and monoclonal antibodies, which are useful in diagnostic assays for detecting PAPAI protein expression as described below or as agonists and antagonists capable of enhancing or inhibiting PAPAI protein function. Further, such polypeptides can be used in the yeast two-hybrid system to "capture" PAPAI protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate PAPAI-specific antibodies include: a polypeptide comprising amino acid residues from about 6 to about 16 in SEQ ID NO:2; a polypeptide comprising amino acid residues from about 31 to about 36 in SEQ ID NO:2; a polypeptide comprising amino acid residues from about 46 to about 76 in SEQ ID NO:2; a polypeptide comprising amino acid residues from about 111 to about 121 in SEQ ID NO:2; a polypeptide comprising amino acid residues from about 146 to about 161 in SEQ ID NO:2; a polypeptide comprising amino acid residues from about 206 to about 211 in SEQ ID NO:2; a polypeptide comprising amino acid residues from about 236 to about 246 in SEQ ID NO:2; a polypeptide comprising amino acid residues from about 306 to about 316 in SEQ ID NO:2; a polypeptide comprising amino acid residues from about 361 to about 366 in SEQ ID NO:2; a polypeptide comprising amino acid residues from about 2 to about 12 in SEQ ID NO:13; a polypeptide comprising amino acid residues from about 27 to about 32 in SEQ ID NO:13; a polypeptide comprising amino acid residues from about 42 to about 72 in SEQ ID NO:13; a polypeptide comprising amino acid residues from about 107 to about 117 in SEQ ID NO:13; a polypeptide comprising amino acid residues from about 142 to about 157 in SEQ ID NO:13; a polypeptide comprising amino acid residues from about 202 to about 207 in SEQ ID NO:13; a polypeptide comprising amino acid residues from about 232 to about 242 in SEQ ID NO:13; a polypeptide comprising amino acid residues from about 302 to about 312 in SEQ ID NO:13; and a polypeptide comprising amino acid residues from about 357 to about 362 in SEQ ID NO:13. As indicated above, the inventors have determined that the above polypeptide fragments are antigenic regions of the PAPAI gene.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, PAPAI polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric PAPAI protein or protein fragment alone (Fountoulakis et al., *J. Biochem* 270:3958–3964 (1995)).

Diagnostic and Prognostic Applications of PAPAI

The present inventors believe that PAPAI is involved in inhibition of the plasminogen activator system. For a number of pathologic disorders, including tumor invasion and metastasis, inflammation, and complications of pregnancy, it is believed that significantly altered levels of PAPAI gene expression can be detected in body tissue or fluids taken from an individual having such a disorder. The level of PAPAI gene expression is measured relative to a "standard" PAPAI gene expression level, i.e., the PAPAI expression level in tissue or fluids from an individual not having the pathologic disorder. Thus, the invention provides a diagnostic method useful during diagnosis of a pathologic disorder, which involves assaying the expression level of the gene encoding the PAPAI protein in tissue or body fluid from an individual and comparing the gene expression level with a standard PAPAI gene expression level, whereby an increase or decrease in the gene expression level over the standard is indicative of a pathologic disorder.

For example, substantial alterations in PAPAI expression or activity can serve as markers of tumor invasiveness and metastasis. This is because PAPAI regulates the fibrinolytic system. Angiogenesis, the growth of new vascular tissue, is regulated by a balance between coagulation and fibrinolysis. Angiogenesis is essential for the expansion of a primary tumor and is also required for the growth of established metastases at distant sites (Holmgren, L. et al., *Nature Medicine* 1:149–153 (1995)). The level of PAI-1 in tumors indicates the level of vascularization, and highly vascularized tumors have higher chances of invasion and metastasis (Fazioli, F. et al., *Trends Pharm. Sci.* 15:25–29 (1995)). Overexpression of PAI-2 in malignant melanoma cells inhibits metastasis in vivo (Mueller, B. M. et al., *Pro. Natl. Acad. Sci. USA* 92:205–209 (1995)). The present inventors have shown that PAPAI is expressed in myoepithelial cells surrounding normal mammary glands and in benign lesions, but not in infiltrating breast carcinomas. Thus, the invention provides a method for predicting whether a tumor is likely to remain stable or will invade tissue and ultimately metastasize. As a result, decisions about whether to pursue relatively invasive clinical interventions, such as surgery, rather than relatively non-invasive interventions, such as chemotherapy and radiation therapy, can be rationally made. The terms "tumor invasiveness" and metastasis are well understood by those of ordinary skill in the art. For example, see Holmgren et al., Fazioli et al., and Mueller et al., supra.

Substantial alterations in PAPAI expression or activity can be used to predict whether hemorrhage is likely to occur in patients who suffer from hepatic illnesses. Alcoholic cirrhosis, primary biliary cirrhosis, and liver cancer are all diseases which are accompanied by hemorrhage due to fibrinolytic bleeding. That is, the bleeding which occurs is not due to injury, but rather is due to a dysregulated fibrinolytic system. The overall level of plasminogen activator activity represents a balance between the relative levels of activator and inhibitor. Changes in PAPAI activity, or a difference in the ratio of plasminogen activator to PAPAI can serve as indicators of imminent hemorrhage in patients who suffer from alcoholic cirrhosis, primary biliary cirrhosis, and liver cancer. Thus, the invention further provides a method for predicting whether hemorrhage will occur in such patients. The terms "hemorrhage," "alcoholic cirrhosis," "primary biliary cirrhosis," "liver cancer, and "fibrinolytic bleeding" are well understood by those of ordinary skill in the art. For example, see Leiper, K. et al., *J. Clin. Pathol.* 47:214–217 (1994).

Substantial alterations in PAPAI expression or activity can be used to predict whether a patient is likely to develop preeclampsia. Preeclampsia is a clinical syndrome that affects women in the third trimester of pregnancy. The syndrome is characterized by hypertension and proteinuria. The etiology of this obstetric complication is unknown. However, it is associated with fibrin deposition in the subendothelium of the renal glomerulus and in the decidua segments of spiral arteries. In fatal cases of eclampsia, widespread fibrin deposition has been a prominent histologic finding. Changes in PAPAI activity, or a difference in the ratio of plasminogen activator to PAPAI can serve as indicators of an imminent advance from the pre-eclamptic to the eclamptic state in patients who are at risk for eclampsia. Thus, the invention further provides a method for predicting whether a pre-eclamptic patient is at risk for developing eclampsia. The term "preeclampsia" is well understood by those of ordinary skill in the art. For example, see Koh, C. L. et al., *Gynecol. Obstet. Invest.* 35:214–221 (1993).

Alterations in PAPAI expression can be assayed at the level of messenger RNA transcription or protein expression. Suitable assay techniques are disclosed below. Alternatively, PAPAI inhibitory activity can be assayed using a spectrophotometric plasminogen activator inhibitor assay. Such an assay is well-known to those of ordinary skill in the art. For example, see Erikkson, E. et al., *Thrombosis Research* 50:91–101 (1988).

By individual is intended mammalian individuals, preferably humans. By "measuring the expression level of the gene encoding the PAPAI protein" is intended qualitatively or quantitatively measuring or estimating the level of the PAPAI or the level of the mRNA encoding the PAPAI protein in a first biological sample either directly (e.g., by determining or estimating absolute protein level or mRNA level) or relatively (e.g., by comparing to the PAPAI protein level or mRNA level in a second biological sample). Preferably, the PAPAI protein level or mRNA level in the first biological sample is measured or estimated and compared to a standard PAPAI protein level or mRNA level, the standard being taken from a second biological sample obtained from an individual not having the disorder or being determined by averaging levels from a population of individuals not having the disorder. As will be appreciated in the art, once a standard PAPAI protein level or mRNA level is known, it can be used repeatedly as a standard for comparison.

By "biological sample" is intended any biological sample obtained from an individual, a cell line, a tissue culture, or other source which contains PAPAI protein or mRNA, secretes mature PAPAI protein, or expresses the PAPAI receptor. Biological samples include normal tissue or cells and tumor cells (whether malignant or benign). Biological samples include body fluids, including whole blood, serum, plasma, urine, saliva, tears, pulmonary secretions, gastrointestinal secretions, fecal material, lymph fluid, synovial fluid, and cerebrospinal fluid. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the PAPAI protein are then assayed using any appropriate method. These include Northern blot analysis, S1 nuclease mapping, the polymerase chain reaction (PCR), reverse transcription (RT) in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. PAPAI protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the PAPAI protein). Northern blot analysis can be performed as described above.

Preferably, levels of mRNA encoding the PAPAI protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the PAPAI protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying PAPAI protein levels in a biological sample can occur using any art-known method. Preferred for assaying PAPAI protein levels in a biological sample are antibody-based techniques. For example, PAPAI protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of PAPAI protein for Western-blot or dot/slot assay (Jalkanen, M., et al., *J. Cell. Biol.* 101:976–985 (1985)); Jalkanen, M., et al., *J. Cell. Biol.* 105:3087–3096 (1987)). In this technique, which is based on the use of cationic solid phases, quantitation of PAPAI protein can be accomplished using isolated PAPAI protein as a standard. This technique can also be applied to body fluids. With these samples, a molar concentration of PAPAI protein will aid to set standard values of PAPAI protein content for different body fluids, like serum, plasma, urine, synovial fluid, spinal fluid, etc. The normal appearance of PAPAI protein amounts can then be set using values from healthy individuals, which can be compared to those obtained from a test subject.

Other antibody-based methods useful for detecting PAPAI protein levels include immunoassays, such as the enzyme linked immunoadsorbent assay (ELISA) and the radioimmunoassay (RIA). For example, PAPAI protein-specific monoclonal antibodies can be used both as an immunoadsorbent and as an enzyme-labeled probe to detect and quantify the PAPAI protein. The amount of PAPAI protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect PAPAI protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting PAPAI protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying PAPAI protein levels in a biological sample obtained from an individual, PAPAI protein can also be detected in vivo by imaging. Antibody labels or markers for in vivo imaging of PAPAI protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A PAPAI protein-specific antibody or antibody portion which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}$Tc. The labeled antibody or antibody portion will then preferentially accumulate at the location of cells which contain PAPAI protein. In vivo tumor imaging is described in S. W. Burchiel et al., "Immunopharmacokinetics of Radiolabeled Antibodies and Their Portions" (Chapter 13 in *Tumor Imaging: The Radiochemical Detection of Cancer*, eds., S. W. Burchiel and B. A. Rhodes, Masson Publishing Inc. (1982)).

PAPAI protein-specific antibodies for use in the present invention can be raised against the intact PAPAI protein or an antigenic polypeptide portion thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody portions (such as, for example, Fab and F(ab')$_2$ portions) which are capable of specifically binding to PAPAI protein. Fab and F(ab')$_2$ portions lack the Fc portion of intact antibody, clear more rapidly from the circulation, and may have less non-specific tissue binding of an intact antibody (Wahl et al., *J. Nucl. Med.* 24:316–325 (1983)). Thus, these portions are preferred.

The antibodies of the present invention may be prepared by any of a variety of methods. For example, cells expressing the PAPAI protein or an antigenic portion thereof can be administered to an animal in order to induce the production of sera containing polyclonal antibodies. In a preferred method, a preparation of PAPAI protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies (or PAPAI protein binding portions thereof). Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., In: Monoclonal Antibodies and T-Cell Hybridomas, Elsevier, N.Y., pp. 563–681 (1981)). In general, such procedures involve immunizing an animal (preferably a mouse) with a PAPAI protein antigen or, more preferably, with a PAPAI protein-expressing cell. Suitable cells can be recognized by their capacity to bind PAPAI protein antibody. Such cells may be cultured in any suitable tissue culture medium; however, it is preferable to culture cells in Earle's modified Eagle's medium supplemented with 10% fetal bovine serum (inactivated at about 56 □C), and supplemented with about 10 µg/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the PAPAI antigen.

Alternatively, additional antibodies capable of binding to the PAPAI protein antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, PAPAI protein specific antibodies are used to immunize an animal, preferably a mouse. The splenocytes of such an animal are then used to produce hybridoma cells, and the hybridoma cells are screened to identify clones which produce an antibody whose ability to bind to the PAPAI protein-specific antibody can be blocked by the PAPAI protein antigen. Such antibodies comprise anti-idiotypic antibodies to the PAPAI protein-specific antibody and can be used to immunize an animal to induce formation of further PAPAI protein-specific antibodies.

It will be appreciated that Fab and F(ab')$_2$ and other portions of the antibodies of the present invention may be used according to the methods disclosed herein. Such portions are typically produced by proteolytic cleavage, using enzymes such as papain (to produce Fab portions) or pepsin (to produce F(ab')$_2$ portions). Alternatively, PAPAI protein-binding portions can be produced through the application of recombinant DNA technology or through synthetic chemistry.

Where in vivo imaging is used to detect enhanced levels of PAPAI protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

Further suitable labels for the PAPAI protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{58}$Fe, $^{75}$e, $^{152}$Eu, $^{90}$Y, $^{67}$CU, $^{217}$Ci, $^{211}$At, $^{212}$Pb, $^{47}$Sc, $^{109}$Pd, ect. $^{111}$In is a preferred isotope where in vivo imaging is used since its avoids the problem of dehalogenation of the $^{125}$I, or $^{131}$I-labeled monoclonal antibody by the liver. In addition, this radio nucleotide has a more favorable gamma emission energy for imaging (Perkins et al., Eur. J. Nucl. Med. 10:296–301 (1985); Carasquillo et al., J. Nucl. Med. 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861–870 (1987)).

Examples of suitable non-radioactive isotopic labels include $^{57}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al. (Clin. Chim. Acta 70:1–31 (1976)), and Schurs et al. (Clin. Chim. Acta 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a PAPAI protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Therapeutic Uses of PAPAI

As discussed above, the PAPAI-protein is believed to be involved in inhibition of the plasminogen activator system and plays a role in a wide variety of physiologic and pathologic processes. Accordingly, the PAPAI protein has application to any physiologic or pathologic disease condition in which abnormal activity of the plasminogen activator system is implicated and has pathological or physiological consequences. A large number of disease conditions are associated with modifications of the plasminogen activator system (Kruithof et al., *Thromb. Haemost.* 59:7 (1988)). Examples of such disease conditions include, but are not limited to: complications of pregnancy, such as preeclampsia and intrauterine growth retardation (Halligan et al., *Br. Obstet. Gyneco.,* 101:488 (1994); Gilabert et al., *Gynecol. Obstet. Invest.* 38:157(1994)); cancer (Dano et al., *Fibrinolysis* 8:189 (1994); Fazoli, F. et al., *Trends Pharmacol. Sci.* 15:25 (1994); Shinkfield et al., *Fibrinolysis* 6:59 (1992)); and wound healing (Schäfer et al., *Amer. J. Pathol.* 144:1269 (1994)). Because of the role of the plasminogen activator system in these disease states, inhibition of the PA system by PAPAI should provide therapeutic benefits to an individual suffering from one (or more) of these physiologic or pathologic diseases.

Given the fibrinolytic activities modulated by PAPAI, it is readily apparent that a substantially altered level of expression of PAPAI in an individual, compared to the standard or "normal" level, produces pathological conditions such as those described above in relation to diagnosis. It will also be appreciated by one of ordinary skill that, since the PAPAI protein of the invention is translated with a leader peptide suitable for secretion of the mature protein from the cells which express PAPAI, when PAPAI protein (particularly the mature form) is added from an exogenous source to cells, tissues or the body of an individual, the protein will exert its modulating activities on any of its target cells of that individual. Therefore, it will be appreciated that conditions caused by a decrease in the standard or normal level of PAPAI activity in an individual, can be treated by administration of PAPAI protein. Thus, the invention also provides a method of treatment of an individual in need of an increased level of activity comprising administering to such an individual a pharmaceutical composition comprising an amount of an isolated PAPAI polypeptide of the invention, particularly a mature form of the PAPAI protein of the invention, effective to increase the PAPAI activity level in such an individual.

For example, since plasminogen activator inhibitors inhibit tumor cell invasion and metastasis, the invention provides a method for treating or preventing tumor invasion and metastasis in cancers including, but not limited to, leukemia, lung cancer, breast cancer, endometrial and ovarian cancer, melanoma, and gastrointestinal cancers, including pancreatic cancer and colorectal cancer. The present inventors have shown, in an animal model, that the presence of PAPAI alters the invasive potential of breast cancer cells.

In addition, since plasminogen activator inhibitors inhibit fibrinolysis, the invention provides a method for treating or preventing coagulation disorders including, but not limited to, arterial thrombi, venous thrombi, disseminated intravascular coagulation, and excessive bleeding caused by the administration of a pharmaceutical plasminogen activator (such as urokinase or tissue plasminogen activator).

Further, since protease inhibitors are effective antiviral agents, the invention provides a method for treating or preventing infections caused by viruses including, but not limited to, Human Immunodeficiency Virus 1 (HIV-1), HIV-2, hepatitis A, hepatitis B, hepatitis C, hepatitis E, hepatitis F, and hepatitis G.

One of ordinary skill will appreciate that effective amounts of the PAPAI polypeptides for treating an individual in need of an increased level of PAPAI activity (including amounts of PAPAI polypeptides effective for the conditions discussed above, with or without other or plasminogen activator inhibitors or other agents) can be determined empirically for each condition where administration of PAPAI is indicated.

The polypeptide having PAPAI activity may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts.

The PAPAI composition to be used in the therapy will be formulated and dosed in a fashion consistent with good medical practice, taking into account the clinical condition of the individual patient (especially the side effects of treatment with PAPAI alone), the site of delivery of the PAPAI composition, the method of administration, the scheduling of administration, and other factors known to practitioners. The "effective amount" of PAPAI for purposes herein (including a PAPAI effective amount) is thus determined by such considerations.

As a general proposition, the total pharmaceutically effective amount of the PAPAI administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day. If given continuously, the PAPAI is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution or bottle solution may also be employed.

A course of PAPAI treatment to affect the fibrinolytic system appears to be optimal if continued longer than a certain minimum number of days, 7 days in the case of the mice. The length of treatment needed to observe changes and the interval following treatment for responses to occur appears to vary depending on the desired effect.

The PAPAI is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release PAPAI compositions also include liposomally entrapped PAPAI. Liposomes containing PAPAI are prepared by methods known per se: DE 3,218,121; Epstein, et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal PAPAI therapy.

For parenteral administration, in one embodiment, the PAPAI is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the PAPAI uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

PAPAI is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of PAPAI salts.

PAPAI to be used for therapeutic administration must be sterile. Sterility is readily accomplished by filtration through sterile filtration membranes (e.g., 0.2 micron membranes). Therapeutic PAPAI compositions generally are placed into a container having a sterile access port, for example, an intravenous solution bag or vial having a stopper pierceable by a hypodermic injection needle.

PAPAI ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous PAPAI solution, and the resulting mixture is lyophilized. The infusion solution is prepared by reconstituting the lyophilized PAPAI using bacteriostatic Water-for-Injection.

Dosaging may also be arranged in a patient specific manner to provide a predetermined concentration of an PAPAI activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

Pharmaceutical compositions of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The PAPAI polypeptide may also be employed in accordance with the present invention by expression of such polypeptides in vivo or ex vivo, which is often referred to as "gene therapy". Gene therapy with the PAPAI polypeptide is accomplished by introduction of a recombinant vector containing a polynucleotide encoding the PAPAI polypeptide into cells, either in vivo or ex vivo. Methods for preparing recombinant vectors are well known in the art and described, for example, in *Molecular Cloning, A Laboratory Manual*, 2nd. edition, edited by Sambrook, J., Fritsch, E. F. and Maniatis, T., (1989), Cold Spring Harbor Laboratory Press Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by infection with a recombinant viral particle encoding a polypeptide of the present invention. Cells may also be engineered by other techniques, including introduction of recombinant plasmid vectors by means of liposomes, electroporation, microinjection, or calcium phosphate precipitation.

Similarly, cells may be engineered in vivo for expression of a polypeptide in vivo by, for example, procedures known in the art. A recombinant viral or plasmid vector containing the polynucleotide encoding the PAPAI polypeptide is introduced into the target cell. Viral vectors useful in the invention include retroviral vectors, adenoviral vectors, HSV-based vector systems, vaccinia vectors, papovaviruses, and adeno-associated virus.

Delivery of retroviral vectors can be accomplished either by direct infection of target; or by injection of a viral producing cell line for replication-deficient retroviruses, which provides a continuous source of vector particles. Plasmid vectors can be administered in vivo by liposomes, direct injection, and receptor-mediated nucleic acid transfer. Preferred delivery methods include those that target the specific tissue to be treated. For example, for the treatment of breast cancer, receptor-mediated gene transfer by conjugation of the plasmid vector to estrogen via polylysine is one preferred method of delivery (EP 785216).

The nucleic acid sequence encoding the polypeptide of the present invention is under the control of a suitable promoter. Suitable promoters which may be employed include, but are not limited to, the retroviral LTR; the SV40 promoter; the human cytomegalovirus (CMV) promoter; adenovirus promoters; the respiratory syncytial virus promoter; thymidine kinase promoters; inducible promoters, such as the MMT promoter, the metallothionein promoter; heat shock promoters, and cellular promoters including, but not limited to, the histone, pol III, and β-actin promoters. Preferred promoters are those that are active only in the target cell. For example, for treatment of breast cancer, preferred promoters include the DF3/MUC1 promoter (Manome, Y. et al., *J. Biol. Che*, 271: 10560–10568 (1996), the mouse mammary tumor virus long terminal repeat (Holt et al., *Human Gene Therapy* 7:1367–1380 (1996), and the whey acid protein promoter (Doppler, W. et al., *Mol. Endocrinol.* 5:1524–1632 (1991)).

Having generally described the invention, the same will be more readily understood by reference to the following examples, which are provided by way of illustration and are not intended as limiting.

EXAMPLES

Example 1

Expression and Purification of PAPAI in *E. coli*

The DNA sequence encoding the mature PAPAI protein in the deposited cDNA clone is amplified using PCR oligonucleotide primers specific to the amino acid carboxyl terminal sequence of the PAPAI protein and to vector sequences 3' to the gene. Additional nucleotides containing restriction sites to facilitate cloning are added to the 5' and 3' sequences, respectively.

The 5' oligonucleotide primer has the sequence 5' CGC <u>CCA TGG</u> GAA GTC AAG CCT CAA G 3' (SEQ ID NO:5) containing the underlined Nco I restriction site (which encodes a start ATG within the Nco I site), followed by 16 nucleotides complementary to bp 110–125 of the antisense strand of the PAPAI protein coding sequence set out in FIGS. 1A–1B (SEQ ID NO:1).

The 3' primer has the sequence 5'CGC <u>AAG CTT</u> TCA CTT CCT TTT ATC TCC CTG 3' (SEQ ID NO:6) containing the underlined Hind III restriction site, followed by 8 nucleotides complementary to bp 1250–1267 of the sense strand of the PAPAI protein coding sequence set out in FIGS. 1A–1B (SEQ ID NO:1), and a stop codon.

The restrictions sites are convenient to restriction enzyme sites in the bacterial expression vector pQE-60, which is used for bacterial expression in these examples. (Qiagen, Chatsworth, Calif., 91311).

The amplified PAPAI protein DNA and the vector pQE-60 are both digested with Nco I and Hind III and the digested DNAs are subsequently ligated together. Insertion of the PAPAI protein DNA into the pQE-60 restricted vector places the PAPAI protein coding region downstream of and operably linked to the vector's promoter and in-frame with an initiating AUG appropriately positioned for translation of PAPAI protein.

The ligation mixture is transformed into competent *E. coli* cells using standard procedures. Such procedures are described, for example, in Sambrook et al., *Molecular Cloning: A Laboratory Manual*, 2nd Ed., Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), is used in carrying out the illustrative example described here. This strain, which is only one of many that are suitable for expressing PAPAI protein, is available commercially from Qiagen.

Transformants are identified by their ability to grow on LB plates in the presence of ampicillin. Plasmid DNA is isolated from resistant colonies and the identity of the cloned DNA is confirmed by restriction analysis.

Clones containing the desired constructs are grown overnight ("ON") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") are then added to a final concentration of 1 mM to induce transcription from lac repressor sensitive promoters, by inactivating the lac repressor. Cells subsequently are incubated further for 3 to 4 hours. Cells are then harvested by centrifugation and disrupted, by standard methods. Inclusion bodies are purified from the disrupted cells using routine collection techniques, and protein are solubilized from the inclusion bodies into 8 M urea. The 8 M urea solution containing the solubilized protein is passed over a PD-10 column in 2× phosphate buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2× PBS at a concentration of 95 micrograms per mL.

Analysis of the preparation by standard methods of polyacrylamide gel electrophoresis reveals that the preparation contains about 95% monomer PAPAI protein having the expected molecular weight of approximately 44.5 kDa.

Example 2

Cloning and Expression in Mammalian Cells

Most of the vectors used for the transient expression of the PAPAI protein gene sequence in mammalian cells should carry the SV40 origin of replication. This allows the replication of the vector to high copy numbers in cells (e.g., COS cells) which express the T-antigen required for the initiation of viral DNA synthesis. Any other suitable mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTL VI, HIVI and the early promoter of the cytomegalovirus (CMV). Cellular signals may, however, also be used (e.g., human actin, promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that may be used include human Hela, 283, H9 and Jurkart cells, mouse NIH3T3 and C127 cells, Cos 1, Cos 7 and CV1 African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 438:4470 (1985)) plus a fragment of the CMV-enhancer (Boshart et al., *Cell* 41:521–530 (1985)). Multiple cloning sites, such as the restriction enzyme cleavage sites BamHI, XbaI and Asp718, facilitate the cloning of the gene of interest. These vectors contain, in addition to the 3' intron, the polyadenylation and termination signal of the rat preproinsulin gene.

Example 2(a)

Expression and Purification of Human PAPAI Protein using the CHO Expression System The vector pC1 is used for the expression of PAPAI protein. Plasmid pC1 is a derivative of the plasmid pSV2-dhfr (ATCC Accession No. 37146). Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3□ intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTL VI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding PAPAI protein in the deposited polynucleotide is amplified using PCR oligonucleotide primers specific to the carboxyl terminal sequence of the PAPAI protein and to vector sequences 3' to the gene. Additional nucleotides containing restriction sites to facilitate cloning are added to the 5' and 3' sequences respectively.

The 5' primer has the sequence 5'CGC <u>GGA TCC</u> GCC ATC ATG GAC ACA ATC TTC TTG 3' (SEQ ID NO:7) containing the underlined Bam HI restriction enzyme site, followed by 16 nucleotides complementary to bp 67–84 of the antisense strand of the PAPAI protein coding sequence set out in FIGS. 1A–1B (SEQ ID NO:1). For the full length gene, the 3' primer has the full length sequence CGC <u>GGT ACC</u> TCA CTT CCT TTT ATC TCC CTG (SEQ ID NO:8), containing the underlined Asp718 restriction site, followed by 8 nucleotides complementary to bp 1250–1267 of the sense strand of the PAPAI protein coding sequence set out in FIGS. 1A–1B (SEQ ID NO:1), and a stop codon.

The restrictions sites are convenient to restriction enzyme sites in the CHO expression vector CHO-1. The amplified PAPAI protein DNA and the vector CHO-1 both are digested with BamH I and Asp718 and the digested DNAs subsequently ligated together. Insertion of the PAPAI protein DNA into the BamH I/Asp718 digested vector places the PAPAI protein coding region downstream of and operably linked to the vector's promoter. The ligation mixture is transformed into E. coli strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the PAPAI-encoding fragment.

Transfection of CHO-DHFR-cells

Chinese hamster ovary cells lacking an active DHFR enzyme are used for transfection. 5 μg of the expression plasmid C1 are cotransfected with 0.5 μg of the plasmid pSVneo using the lipofectin method (Feigner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

Example 2(b)

Expression and Purification of Human PAPAI Protein Using the COS Expression System The expression plasmid, pPAPAI HA, is made by cloning a cDNA encoding PAPAI into the expression vector pcDNAI/Amp (which can be obtained from Invitrogen, Inc.).

The expression vector pcDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire PAPAI precursor and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows. The PAPAI cDNA of the deposited clone is amplified using primers that contain convenient restriction sites, much as described above regarding the construction of expression vectors for expression of PAPAI in E. coli. To facilitate detection, purification and characterization of the expressed PAPAI, one of the primers contains a hemagglutinin tag ("HA tag") as described above.

Suitable primers include that following, which are used in this example. The 5' primer has the sequence 5'CGC <u>GGA TCC</u> GCC ATC ATG GAC ACA ATC TTC TTG 3' (SEQ ID NO:7) containing the underlined BamH I restriction enzyme site, followed by 16 nucleotides complementary to bp 67–84 of the antisense strand of the PAPAI protein coding sequence set out in FIGS. 1A–1B (SEQ ID NO:1). For the full length gene, the 3' primer has the full length sequence CGC <u>TCT AGA</u> TCA AGC GTA GTC TGG GAC GTC GTA TGG GTA GGG ATT TGT CAC TCT TCC (SEQ ID NO:9), containing the underlined Xba I restriction site, an HA tag, and 18 nucleotides complementary to bp 1225–1242 of the sense strand of the PAPAI protein coding sequence set out in FIGS. 1A–1B (SEQ ID NO:1).

The PCR amplified DNA fragment and the vector, pcDNAI/Amp, are digested with BamH I and Xba I and then ligated. The ligation mixture is transformed into E. coli strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the PAPAI-encoding fragment.

For expression of recombinant PAPAI, COS cells are transfected with an expression vector, as described above, using DEAE-DEXTRAN, as described, for instance, in Sambrook et al., *Molecular Cloning: A Laboratory Manual*, Cold Spring Laboratory Press, Cold Spring Harbor, N.Y. (1989). Cells are incubated under conditions for expression of PAPAI by the vector.

Expression of the PAPAI HA fusion protein is detected by radiolabelling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}S$-cysteine for 8 hours. The cells and the media are collected, and the cells are washed and the lysed with detergent-containing RIPA buffer: 150 mM NaCl, 1% NP-40, 0.1% SDS, 1% NP-40,0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3

Cloning and Expression of the PAPAI Protein in a Baculovirus Expression System

The cDNA sequence encoding the soluble extracellular domain of PAPAI protein receptor protein in the deposited clone is amplified using PCR oligonucleotide primers corresponding to the 5' and 3' sequences of the gene:

The 5' primer has the sequence 5'CGC <u>GGA TCC</u> GCC ATC ATG GAC ACA ATC TTC TTG 3' (SEQ ID NO:7) containing the underlined BamH I restriction enzyme site followed by 18 bases (bp 67–84) complementary to the antisense strand of the PAPAI protein coding sequence of FIGS. 1A–1B (SEQ ID NO:1). Inserted into an expression vector, as described below, the 5' end of the amplified fragment encoding PAPAI protein receptor provides an efficient signal peptide. An efficient signal for initiation of translation in eukaryotic cells, as described by Kozak, M., *J. Mol. Biol.* 196:947–950 (1987), may be located, as appropriate, in the vector portion of the construct.

For the full length gene, the 3' primer has the full length sequence CGC GGT ACC TCA CTT CCT TTT ATC TCC CTG (SEQ ID NO:8), containing the underlined Asp718 restriction followed by nucleotides complementary to bp 1250–1267 of the sense strand of the PAPAI protein set out in FIGS. 1A–1B (SEQ ID NO:1), and a stop codon.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein F2.

The vector pA2 is used to express the PAPAI protein in the baculovirus expression system, using standard methods, such as those described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa califomica* nuclear polyhedrosis virus (AcMNPV) followed by convenient restriction sites. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described, for example, in Luckow et al., *Virology* 170:31–39 (1989). Suitable vectors will be readily apparent to the skilled artisan.

The plasmid is digested with the restriction enzymes BamHI and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB 101 cells are transformed with ligation mix and spread on culture plates. Bacteria are identified that contain the plasmid with the human PAPAI protein gene by digesting DNA from individual colonies using Bam HI and Asp718 and then analyzing the digestion product by gel electrophoresis. The sequence of the cloned fragment is confirmed by DNA sequencing. This plasmid is designated herein as pBacPAPAI.

5 μg of plasmid pBacPAPAI is co-transfected with 1.0 μg of a commercially available linearized baculovirus DNA ("BaculoGold□ baculovirus DNA", Pharmingen, San Diego, Calif.), using the lipofection method described by Felgner et al., *Proc. Natl. Acad. Sci. USA* 84:7413–7417 (1987). 1 μg of BaculoGold□ virus DNA and 5 μg of the plasmid pBacPAPAI are mixed in a sterile well of a microliter plate containing 50 μl of serum free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27 □C. After 5 hours the transfection solution is removed from the plate and 1 ml of Grace's insect medium supplemented with 10% fetal calf serum is added. The plate is put back into an incubator and cultivation is continued at 27 □C for four days.

After four days the supernatant is collected and a plaque assay is performed, as described by Summers and Smith, supra. An agarose gel with "Blue Gal" (Life Technologies Inc., Gaithersburg, Md.) is used to allow easy identification and isolation of gal-expressing clones, which produce blue-stained plaques. A detailed description of a "plaque assay" of this type can also be found in the user's guide for insect cell culture and baculovirology distributed by Life Technologies Inc., Gaithersburg, Md., at pages 9–10.

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4 □C. A clone containing properly inserted PAPAI protein receptor is identified by DNA analysis including restriction mapping and sequencing. This is designated herein as V-PAPAI.

Sf9 cells are grown in Grace's medium supplemented with 10% heat-inactivated FBS. The cells are infected with the recombinant baculovirus V-PAPAI at a multiplicity of infection ("MOI") of about 2 (about 1 to about 3). Six hours later the medium is removed and is replaced with SF900 II medium minus methionine and cysteine (available from Life Technologies Inc., Gaithersburg, Md.). 42 hours later, 5 μCi of $^{35}$S methionine and 5 MCi $^{35}$S cysteine (available from Amersham) are added. The cells are further incubated for 16 hours and then they are harvested by centrifugation, lysed and the labeled proteins are visualized by SDS-PAGE and autoradiography.

Example 4
Tissue Distribution of PAPAI Protein Expression

Northern blot analysis was carried out to examine the levels of expression of PAPAI protein in human tissues, using methods described by, among others, Sambrook et al, cited above. PolyA$^+$ was purchased from Clontech (1020 East Meadow Circle, Palo Alto, Calif. 94303).

About 1 μg of PolyA$^+$ RNA was size resolved by electrophoresis through a 1% agarose gel under strongly denaturing conditions. RNA was blotted from the gel onto a nylon filter, and the filter then was prepared for hybridization to a detectably labeled polynucleotide probe.

As a probe to detect mRNA that encodes PAPAI protein, the antisense strand of the coding region of the cDNA insert in the deposited clone was labeled to a high specific activity. The cDNA was labeled by primer extension, using the Prime-It kit, available from Stratagene. The reaction was carried out using 50 ng of the cDNA, following the standard reaction protocol as recommended by the supplier. The labeled polynucleotide was purified away from other labeled reaction components by column chromatography using a Select-G-50 column, obtained from 5-Prime —3-Prime, Inc. of 5603 Arapahoe Road, Boulder, Colo. 80303.

The labeled probe was hybridized to the filter, at a concentration of 1,000,000 cpm/ml, as described in Kreider et al., *Molecular and Cellular Biology*, September 1990, pp. 4846–4853. Thereafter the probe solution was drained and the filter was washed twice at room temperature and twice at 65 □C with 0.1×SSC, 0.1% SDS. The filter then was then dried and exposed to film at −70 □C overnight with an intensifying screen.

The Northern blot analysis showed maximal PAPAI transcript levels in pancreas. Adipose also demonstrated a high abundant PAPAI expression. No bands were present in other specimens analyzed, including heart, brain, kidney, liver, lung, spleen, skeletal muscle, esophagus, stomach, intestine, colon, uterus, placenta, bladder, tonsil, thymus, appendix, lymph node, gall bladder, prostate, testis and ovary.

Tissue expression of PAPAI appears to be limited. Although large amounts of transcript were detected in pancreas and adipose by Northern blot, no PAPAI transcript was detected in all other tested tissues including liver and placenta which are the rich sources for PAI-1 and PAI-2 respectively. PAPAI may function in a tissue-specific fashion as part of an acute response to tissue remodeling.

Example 5
Expression of PAPAI Protein in Normal and Cancerous Breast Cells

The expression of PAPAI in human breast cancers was investigated in a variety of human breast cancer cell lines. The RNA from human breast cancer cells was prepared using the RNA isolation kit RNAzol B (Tel-Test, Inc) based on manufacturer's instructions. Equal aliquots of RNA were electrophoresed in a 1.2% agarose gel containing formaldehyde and transferred to a nylon membrane (Boehringer Mannheim). The membrane was pre-hybridized with ExpressHyb hybridization solution (Clontech, Inc.) at 68 □C for 30 min. The hybridization was carried out in the same solution with $^{32}$P-labeled PAPAI probe (1.5×10$^6$ cpm/ml) for 1 hour at 68 □C. The membrane was then rinsed in 2×SSC containing 0.05% SDS three times for 30 min at room temperature followed by two washes with 0.1×SSC containing 0.1% SDS for 40 min at 55 □C. The full-length PAPAI cDNA was isolated from the Bluescript vector followed by EcoRI and XhoI digestion and used for preparation of a cDNA probe.

The Northern blot analysis failed to detect the PAPAI transcript in all tested breast cancer cell lines. The inability to pick up the PAPAI mRNA in breast cancer cell lines by Northern blot indicates that the PAPAI gene may be only expressed in myoepithelial cells.

In order to localize the cellular source of PAPAI expression and to assess the biological relevance of PAPAI expression in breast cancer's progression, in situ hybridization was performed on the fixed sections from a variety of different human breast specimens. In this example, two aspects of PAPAI expression were examined, including the tissue localization (stromal versus epithelial) and the potential correlation of the loss of PAPAI expression and breast cancer malignant phenotype. A 1176 bp PAPAI cDNA was inserted into pBluescript SK at unique EcoRI (5') and XhoI (3') sites. The digoxigenin-labeled antisense probe was generated by an EcoRI cut of PAPAI cDNA plasmid and followed by T7 RNA polymerase (Boehringer Mannheim). Deparaffinized and rehydrated tissue sections were treated with 0.2 M HCl at room temperature for 20 min and de-proteinized in 0.2 mg/ml proteinaseK solution at 37 □C for 30 min. The slides were then acetylated in 0.4% acetic anhydride in 0.1M triethanolamine for 10 min and dehydrated in ethanol. Prehybridization was carry out in hybridization buffer (0.3M NaCl, 0.02 Sodium Acetate, 5 mM EDTA, pH 5.0), 50% formamide, 1× Denhardt's, 10% dextran sulfate and 1 mg/ml tRNA over night in a humidity chamber at 50° C. Thereafter, the sections were hybridized with 500 ng/ml DIG-labeled RNA probe in the same components as those in the prehybridization step at 50 □C for 18 h. After hybridization, the slides were then washed with 2×SSC, 0.2×SSC, 0.1×SSC separately at 42 □C for 20 min and treated with Rnase A in 0.1×SSC at 37 □C for 30 min. Digoxigenin detection was performed with mouse anti-digoxigenin antibodies (Boehringer Mannheim) followed by incubation with biotin-conjugated secondary rabbit anti-mouse antibodies (DAKO). The colorimetric detections were performed with a standard indirect streptavidin-biotin immunoreaction method using the Universal LSAB Kit (DAKO) according to the manufacture's instructions.

There was a strongly positive PAPAI hybridization in the myoepithelial cells surrounding the normal mammary glands, benign hyperplasias, and benign fibroadenomas. The expression of PAPAI mRNA was detectable in the myoepithelial cells in all four reduction mammoplasty specimens and in three benign lesions. In contrast, expression of PAPAI was absent in five out of five cases of infiltrating breast carcinomas. No PAPAI expression can be detected in both normal and malignant mammary epithelial cells and in stromal fibroblasts. In all cases a strong PAPAI transcript was found in the endothelial cells of small vessels. These in situ hybridization results are consistent with the Northern blot analysis which showed no PAPAI expression in breast cancer cells.

The loss of PAPAI expression in the malignant breast carcinomas may be due to the loss of putative PAPAI-producing myoepithelial cells during the malignant progression. It is intriguing that these data are different from the previous studies that have linked excessive PAI-1 and PAI-2 expression to breast cancers as compared to normal breast (Duggan, C. et al., *Br. J. Cancer* 76(5):622–627 (1997); Brunner, N. et al., *Cancer Treat. Res.* 71:299–309 (1994); Duffy, M. et al., *Cancer* 62, 531–533 (1988); Duggan, C. et al., *nt. J. Cancer* 61:597–600 (1995); Schmitt, M. et al., *Br. J. Cancer* 76(3):306–311 (1997); Bianchi, E. et al., *Int. J. Cancer* 60:597–603 (1995); and Bouchet, C. et al., *Br. J. Cancer* 69:398–405 (1994)). Both in situ hybridization and immunohistochemical staining have demonstrated a strong PAI-1 expression in the stroma surrounding breast carcinomas or at tumor margins (Bianchi, E. et al., *Int. J. Cancer* 60:597–603 (1995)). In particular, it was extensively demonstrated that the clinical outcome of breast cancer is reversely related to the levels of PAI-1 expression (Liu, G. et al., *Int. J. Cancer* 60:501–506 (1995)). It is not easy to understand why the elevated tumor tissue content of PAI-1 indicates a poor prognosis for the breast cancer patients. One explanation is that, the increased expression of PAI-1 may be reciprocally related to the increased expression of u-PA and ohter proteinases during the tumor-mediated degradation of extracellular matrix. Therefore, this elevated levels of PAI-1 in the stroma adjunct to the invasive breast carcinomas may represent one of the subsequent acute host responses to the remodeling stimuli and try to balance the local tissue degradation, but not as a causative factor. Alternatively, the high level expression of PAI-1 in the breast cancer may favor the proposed co-expression model that uPA and PAI-1 have to be present in the tumor in order to achieve focalized and optimal uPA-R-mediated proteolysis and invasiveness (Dickinson, J.-L. et al., *J. Biol. Chem.* 270:27894–27904 (1995)).

PAI-2 most probably is acting on tumor cells in a different way than PAI-1. In contrast to PAI-1, although the PAI-2 expression is also increased in breast cancers relative to normal breast, PAI-2 expression is detected predominantly in the malignant breast cancer cells and high levels of PAI-2 has been proposed as a favourable prognostic marker in breast cancer (Duggan, C. et al., *Br. J. Cancer* 76(5) :622–627 (1997)). Since PAI-2 is mainly found as an intracellular protein, this raises a possibility as to its physiological role on protection of the cells from some harmful effects of an intracellular proteinases (Schmitt, M. et al., *Thromb. Haemost.* 78(1):285–296 (1997)). PAI-2 is an important factor in cytoprotection of cell death in TNFα-induced process through inhibition of the proteinases involved in TNFα-mediated apoptosis (Dickinson, J.-L. et al., *J. Biol. Chem.* 270:27894–27904 (1995)). This PAI-2-mediated cytoprotective role resembles the antiapoptotic action of bcl-2 gene which is in close proximity of the PAI-2 gene on chromosome 18 (Dickinson, J.-L. et al., *J. Biol. Chem.* 270:27894–27904 (1995); Bachmann, F., *Thromb. and Haemostas.* 74(1): 172–179 (1995); and Sternlicht, M.-D. & Barsky, S.-H, *Med. Hypoth.* 48:37–46 (1997)). In this regard, the increased expression of PAI-2 in breast cancer cells may be in part responsible for the less apoptotic phenotype of the malignant cancer cells. On the other hand, a secreted glycoslated form of PAI-2 is also present (Bachmann, F., *Thromb. and Haemostas.* 74(1):172–179 (1995)) and may contribute its anti-invasive and anti-metastatic effect through inhibition of PA.

It is interesting to note that PAPAI expression is seen exclusively in the myoepithelial cells which are lost during the breast cancer malignant progression. Myoepithelial cells, normally surrounding ducts of glandular organs such as breast, contribute to the synthesis of a surrounding basement membrane and exert important paracine effects on epithelial mitogenesis and morphogenesis (Sternlicht, M.-D. & Barsky, S.-H *Med. Hypoth.* 48:37–46 (1997)). In normal or non-invasive benign breast, cell-stromal contact is mediated by myoepithelial cells which secrete relatively low levels of matrix-degrading proteinases but relatively high levels of maspin and various other anti-invasive proteinase inhibitors (Sternlicht, M.-D., Safarians, S., Rivera, S.-P. & Barsky, S.-H. *Lab Invest.* 74 (4), 781–796 (1996)). Myoepithelial cells can also induce differentiation of breast cancer cells (Bani, D. et al., *Br. J. Cancer* 70(5):900–904 (1994)) and inhibit tumor cell invasion in vitro (Sternlicht, M.-D. & Barsky, S.-H *Med. Hypoth.* 48:3746 (1997)). The exclusive expression of PAPAI in myoepithelial cells of normal or benign mammary gland may represent one of the major anti-invasive proteinase inhibitors mediated by the host defensive myoepithelial layer in preventing breast cancer malignant progression. In this regard, the expression of PAPAI in myoepithelial cells would create a microenvironment in the epithelial-stromal interface where the inhibitory effect of PAPAI prevents the excessive proteolytic actions and preserve the epithelial-stromal structure integrity. It has been recognized that an intact myoepithelial layer, like an intact extracellular basement, can distinguish benign epithelial proliferations and in situ carcinomas from invasive disease. The exclusive expression of PAPAI in the myoepithelial cells may play a role as an anti-invasive and anti-metastatic phenotype in the myoepithelial layer.

Example 6
Affect of PAPAI on Breast Cancer Progression

Reagents. Restriction enzymes, T7 polymerase, random primer DNA labeling kit, and digoxigenin-labeled nucleotides were obtained from Boehringer Mannhem, Indianapolis. $^{32}$P-dATP was purchased from Amersham.

In vitro assay for cell growth. Exponentially growing cultures of different MDA-MB-435 clones were detached with trypsin, and the trypsin was neutralized with DMEM-10% serum. Cells were counted, diluted, and seeded in triplicate at 3,000 cells per well (24-well plate) in 1 ml DMEM-5% serum. Cell growth was measured using Cell-Titer 96™ Aqueous Non-Radioactive cell proliferation Assay Kit (Promega).

In vitro invasion assay. The modified Boyden chamber invasion assay was performed as previously described (Wang, M. et al., *Oncogene* 14 (23):2767–2774 (1997)).

Tumor growth, lymph node and lung metastasis, and microvessel counts in athymic nude mice. A nude mouse mammary fat pad tumorigenic and metastatic assay was performed as previously described (Shi, Y.-E., *Cancer Res.* 57:759–764 (1997) and Shi, Y.-E. et al., *Cancer Res.* 57(15) :3084–3091 (1997) and Wang, M. et al., *Oncogene* 14(23) :2767–2774 (1997)). Microvessel counts of primary tumors was analyzed as we previously described for TIMP-4 transfected MDA-MB-435 tumor model (Wang, M. et al., *Oncogene* 14(23):2767–2774 (1997)).

Statistical Analysis. Values were expressed as means±standard errors (SEs). Comparisons were made using the two-tailed Student's t-test. Where appropriate, the chi-squared test was used to compare proportions.

Transfection and selection of PAPAI positive clones. Since the expression of PAPAI in the myoepithelial cells may contribute the roles of myoepithelial layer as paracrine cellular suppression of invasion, it was tested whether we can inhibit breast cancer invasion and metastasis by transfection of PAPAI into metastatic breast cancer cells. In order to select a suitable breast cancer cell line for PAPAI gene transfection, a panel of breast cancer cell lines as well as normal mammary epithelial cells were screened for analysis of PAPAI expression. Northern blot analysis failed to detect the PAPAI transcript in MCF-7, T47D, MDAMB-231, MDAMB-435, MDAMB-436, ZR 75–1, Hs578t and BT549 breast cancer cell lines and NME4144 and NME4244 normal mammary epithelial cells. The inability to pick up the PAPAI mRNA in both normal and malignant breast epithelial cells by Northern blot supports the in situ hybridization data indicating the myoepithelial expression of the PAPAI.

MDA-MB-435 cell line was selected as recipient for PAPAI mediated gene transfection because: 1) it lacks detectable PAPAI transcript; and 2) it is relatively highly tumorigenic and metastatic in nude mice. Human PAPAI cDNA was subcloned into the pCI-neo mammalian expression vector (Promega) downstream of the human cytomegalovirus promoter and enhancer to generate the pCNPAI expression vector. 40 µg pCNPAI or the control vector pCI-neo were used for transfections. 1×10$^6$ MDA-MB-435 human breast cancer cells were plated 24 h prior to transfection on 100-mm dishes and then incubated with IMEM supplemented with 10% FBS, 100 IU/ml penicillin G, 100 mg/ml streptomycin and 2 mM/ml L-glutamine (GIBCO, BRL). Transfection was carried out using the calcium phosphate coprecipitation method. DNA was removed 16 h later by replacing the incubation medium. 24 h later, the cells were subcultured to five 100-mm dishes containing IMEM supplemented with 10% FBS, 100 IU/ml penicillin G, 100 mg/ml streptomycin, 2 mM/ml L-glutamine and 0.8 mg/ml G418 (Geneticin, GIBCO). After colonies of about 104 cells had grown, 30 G418-resistant individual clones were picked and subcloned. Clones were initially screened by in situ hybridization on slides with a specific PAPAI antisense probe, and the positive clones were subjected to Northern blot analysis. MDA-MB-435 subclones transfected with PAPAI cDNA were designated PAPAI-435, and MDA-MB-435 subclones transfected with pCI-neo were designated neo-435. Five PAI-435 clones were picked up by in situ hybridization. All five selected PAI-435 clones, PAI-435-1, PAI-435-5, PAI-435-6, PAI-435-10, and PAI-435-11 expressed PAI mRNA transcripts. In contrast, none of the parental MDA-MB-435 cells or cells transfected with plasmid vector alone produced any detectable PAPAI transcripts.

Expression of plasminogen activator inhibitor activity. The anti-tPA activity of PAPAI transfected clones was characterized. Conditioned media from two PAI-435 clones, one control clone and parental MDA-MB-435 cells were collected, concentrated, and analyzed for plasminogen activator inhibitory activity. Although the basal level PAI-like activities were detected in PAPAI negative clones, the anti-tPA activities in two PAPAI positive clones were three times higher than that of PAPAI negative clones. These results indicate that the PAPAI transfected clones secreted a functional PAPAI protein.

In vitro growth of PAPAI-435 cells. To determine whether PAPAI expression affects the growth of MDA-MB-435 cells, the growth rates of PAPAI-435-1 and PAPAI-435-10 cells were compared to that of neo-435-2 and neo-4354 cells in the monolayer culture. No significant differences in growth rate were observed among PAPAI positive and PAPAI negative cells.

Effect of PAPAI transfection on tumorigenicity. To study the effect of PAPAI expression on tumorigenicity, picked two PAPAI positive clones were tested: PAPAI-435-1 and PAPAI-435-10; and two PAPAI negative cells: neo-435-2 and neo-435-4. A pilot study was done and the data are summarized in Table 2. After a lag phase of 7–10 days, all the 20 injections in the mice given implants of PAPAI negative cells developed tumors. In contrast, only 10 injections in the mice given implants of PAPAI positive cells developed tumors. Starting at about 27 days after inoculation, great level of tumor necrosis was observed in tumors derived from neo-435-1 and neo-435-10 cells. The same breast cancer cells transfected with PAPAI, however, were significantly inhibited in their tumor growth; and either no or low level of tumor necrosis was observed. The size of PAPAI-435-10 tumors was only 23% of that in parental neo-435-1 tumors and 21% of that in neo-435-10 tumors. In addition, the tumor incidence was also greatly decreased. With 10 injections, only two implants developed tumors. The tumor growth of PAPAI-435-1 cells was also significantly reduced, with 54% and 52% inhibition of tumor size observed as compared to neo-435-2 and neo-435-15 tumors, respectively.

TABLE 2

Effects of PAPAI expression on tumor sizes and tumor incidence.

| Treatment Group | Tumor vol (mm$^3$) of primary size | Tumor incidence Tumor/Total |
| --- | --- | --- |
| 435-neo-2 | 366.81 ± 75.26 | 10/10 (100%) |
| 435-neo-4 | 387.38 ± 91.72 | 10/10 (100%) |
| PAPAI-435-1 | 199.54 ± 32.88 | 8/10 (80%) |
| PAPAI-435-10 | 83.13 ± 8.41 | 2/10 (20%) |

Discussion

In this example, the biological relevance of PAPAI in human breast cancer progression was characterized. Amino acid sequence analysis indicate that PAPAI shares considerable sequence similarity with members of the serpin family, including PAI-1 and PAI-2. Like PAI-1, a cleavable hydrophobic signal sequence is identified for PAPAI, indicating its secretion. PAPAI expressed in MDA-MB-435 human breast cancer cells. As expected, the resulting recombinant PAPAI protein possesses an inhibitory activity on PA and is secreted extracellularly, thus confirming that the novel protein is a new member of the PAI family.

Transfection of the MDA-MB-435 cells with a PAPAI cDNA leads to increased expression of the PAPAI transcript and anti-tPA activity when compared to parental cell line and control cells. The reduced in vitro invasiveness of PAPAI-435 clones compared to control cells suggests that the production of PAPAI altered the invasive potential of breast cancer cells in this experimental model system. These results are consistent with the previous reports on the inhibition of the invasion by PAI-1 (Soff, G.-A. et al., *J. Clin. Invest.* 96:2593–2600 (1995)) and PAI-2 (37–38). In our nude mouse model of mammary tumor, overexpression of PAPAI resulted in several phenotypic changes: (a) there was a significant reduction in incidence and size of primary tumors; (b) tumor-associated angiogenesis was inhibited as evidenced by the reduced microvessel density in the tumor; (c) the number of microscopic metastatic lesions in the lung and lymph node was reduced. The PAPAI-mediated in vivo tumor growth inhibition is somewhat conflicting to the in vitro similar growth rates of PAPAI-positive clones compared to PAPAI-negative clones. The slower in vivo growth of PAPAI-435 tumors may be explained, in part, by PAPAI-mediated inhibition of tumor angiogenesis. Angiogenic regulatory factors have been found to modulate the growth of human breast cancers in several orthotopic xenograft models. We have recently demonstrated that transfection of MDA-MB-435 cells with an angiogenic factor Scatter Factor (SF) increased tumor growth and angiogenesis (Mignati, P., Tsuboi, R., Robbins, E. & Rifkin, D.-B. *J. Cell Biol.* 108,671–682 (1989)); in contrast, overexpression of tissue inhibitor of metalloproteinase 4 (TIMP-4) in MDA-MB-435 cells inhibited primary tumor growth, metastasis, and tumor angiogenesis (Wang, M. et al., *Oncogene* 14 (23) :2767–2774 (1997)). The data in this example indicate that despite the lack of growth inhibition of PAPAI on breast cancer cells, PAPAI significantly inhibits tumor growth and metastasis presumably due to its anti-angiogenic activity. In fact, uPA stimulates components of angiogenesis including chemotaxis, proteolytic matrix degradation, and the release of basic fibroblast growth factor from its storage in the basement membrane (Yasunaga, C. et al., *Lab. Invest.* 61:689–704 (1989); Mignati, P. et al., *J. Cell Biol.* 108:671–682 (1989); Saksela, O. & Rifkin, D.-B. *J. Cell Biol.* 110: 767–775 (1990); and Flaumenhaft, R. et al., *J. Cell Physiol.* 140:75–81 (1989)). Furthermore, both PAI-1 (Soff, G.-A. et al., *J. Clin. Invest.* 96:2593–2600 (1995)) and PAI-2 have been demonstrated to have an anti-angiogenic activity presumably through inhibition of uPA expressed by endothelial cells in newly forming capillary sprouts.

The magnitude of the tumor-suppressing activity of PAPAI on human breast cancer is greater than that observed previously for metalloproteinase inhibitor TIMP-4 (Wang, M. et al., *Oncogene* 14(23):2767–2774 (1997)) and comparable to that observed for tumor suppressor Rb and p53 (Wang, N.-P. et al., *Oncogene* 8:279–288 (1993)). The exclusive expression of PAPAI in the myoepithelial cells of normal and benign breast and the inhibition of breast tumor growth and metastasis by PAPAI expression suggest that PAPAI is one of the local myoepithelial-related paracrine factors that preserve the normal epithelial-stromal integrity and prevent the malignant progression from benign or in situ to the metastatic phenotype.

The entire disclosure of each document cited in this application is hereby incorporated herein by reference.

What is claimed is:

1. A method of producing an antibody that specifically binds the polypeptide of SEQ ID NO:2 comprising:
    (a) introducing into an animal a polypeptide comprising an amino acid sequence selected from the group consisting of:
        (i) amino acids −14 to 378 of SEQ ID NO:2;
        (ii) amino acids −13 to 378 of SEQ ID NO:2; and
        (iii) amino acids 1 to 378 of SEQ ID NO:2; and
    (b) recovering said antibody.

2. The method of claim 1 wherein the antibody binds a polypeptide consisting of amino acids −14 to 378 of SEQ ID NO:2.

3. The method of claim 1 wherein the antibody binds a polypeptide consisting of amino acids −13 to 378 of SEQ ID NO:2.

4. The method of claim 1 wherein the antibody binds a polypeptide consisting of amino acids 1 to 378 of SEQ ID NO:2.

5. The method of claim 1 wherein the antibody is a polyclonal antibody.

6. The method of claim 1 that also comprises the step of generating a hybridoma prior to recovering said antibody.

7. The method of claim 6 wherein the antibody is a monoclonal antibody.

8. A method of producing an antibody that specifically binds the full-length polypeptide encoded by the cDNA in American Type Culture Collection (ATCC) Deposit No. 97657 comprising:
    (a) introducing into an animal a polypeptide selected from the group consisting of:
        (i) the full length amino acid sequence as encoded by the cDNA clone contained in ATCC Deposit No. 97657;
        (ii) the mature amino acid sequence as encoded by the cDNA clone contained in ATCC Deposit No. 97657; and
        (iii) full-length protein encoded by the cDNA contained in ATCC Deposit No. 97657, excepting the N-terminal methionine; and
    (b) recovering said antibody.

9. The method of claim 8 wherein the antibody binds a polypeptide consisting of the full length amino acid sequence as encoded by the cDNA clone contained in ATCC Deposit No. 97657.

10. The method of claim 8 wherein the antibody binds a polypeptide consisting of the mature sequence as encoded by the cDNA clone contained in ATCC Deposit No. 97657.

11. The method of claim 8 wherein the antibody binds a polypeptide consisting of the full-length protein encoded by the cDNA contained in ATCC Deposit No. 97657.

12. The method of claim 8 wherein the antibody is a polyclonal antibody.

13. The method of claim 8 that also comprises the step of generating a hybridoma prior to recovering said antibody.

14. The method of claim 13 wherein the antibody is a monoclonal antibody.

15. A method of producing an antibody that specifically binds the polypeptide of SEQ ID NO:2 comprising:
   (a) screening a single chain or Fab expression library to identify an antibody that specifically binds a polypeptide selected from the group consisting of:
       (i) amino acids −14 to 378 of SEQ ID NO:2;
       (ii) amino acids −13 to 378 of SEQ ID NO:2; and
       (iii) amino acids 1 to 378 of SEQ ID NO:2; and
   (b) recovering said antibody from said library.

16. The method of claim 15 wherein the antibody is a single chain antibody.

17. The method of claim 15 wherein the antibody is an Fab fragment.

18. The method of claim 15 wherein the polypeptide consists of amino acids −14 to 378 of SEQ ID NO:2.

19. The method of claim 15 wherein the polypeptide consists of amino acids −13 to 378 of SEQ ID NO:2.

20. The method of claim 15 wherein the polypeptide consists of amino acids 1 to 378 of SEQ ID NO:2.

21. A method of producing an antibody that specifically binds the polypeptide encoded by the cDNA in ATCC Deposit No. 97657 comprising:
   (a) screening a single chain or Fab expression library to identify an antibody that binds a polypeptide selected from the group consisting of:
       (i) the full length amino acid sequence as encoded by the cDNA clone contained in ATCC Deposit No. 97657;
       (ii) the mature amino acid sequence as encoded by the cDNA clone contained in ATCC Deposit No. 97657; and
       (iii) full-length protein encoded by the cDNA contained in ATCC Deposit No. 97657, excepting the N-terminal methionine; and
   (b) recovering said antibody from said library.

22. The method of claim 21 wherein the antibody is a single chain antibody.

23. The method of claim 21 wherein the antibody is an Fab fragment.

24. The method of claim 21 wherein the polypeptide consists of the full length amino acid sequence as encoded by the cDNA clone contained in ATCC Deposit No. 97657.

25. The method of claim 21 wherein the polypeptide consists of the mature amino acid sequence as encoded by the cDNA clone contained in ATCC Deposit No. 97657.

26. The method of claim 21 wherein the polypeptide consists of the full-length protein encoded by the cDNA contained in ATCC Deposit No. 97657, excepting the N-terminal methionine.

* * * * *